(12) United States Patent
Morris et al.

(10) Patent No.: US 6,596,930 B1
(45) Date of Patent: Jul. 22, 2003

(54) MODIFICATION OF CEREAL GRAIN HARDNESS VIA EXPRESSION OF PUROINDOLINE PROTEIN

(75) Inventors: Craig F. Morris, Pullman, WA (US); Michael J. Giroux, Bozeman, MT (US)

(73) Assignees: The United States of America as represented by the Secretary of Agriculture, Washington, DC (US); Montana State University, Bozeman, MT (US)

( * ) Notice: Subject to any disclaimer, the term of this patent is extended or adjusted under 35 U.S.C. 154(b) by 0 days.

(21) Appl. No.: 09/083,852

(22) Filed: May 22, 1998

(51) Int. Cl.$^7$ .............................. A01H 5/00; C12N 5/04; C12N 15/82; C12N 15/84

(52) U.S. Cl. ................. 800/320.1; 800/320; 800/320.2; 800/320.3; 800/298; 800/278; 435/412; 435/419

(58) Field of Search ................................. 800/278, 294, 800/298, 320.3, 320, 320.1, 320.2, 266; 439/469, 419; 435/412

(56) References Cited

U.S. PATENT DOCUMENTS

| | | | |
|---|---|---|---|
| 5,187,073 A | 2/1993 | Goldman et al. | 435/172.3 |
| 5,500,361 A | 3/1996 | Kinney | 435/172.3 |

OTHER PUBLICATIONS

Cheng, M. et al., "Genetic Transformation of Wheat Mediated by Agrobacterium tumefaciens." 1997, Plant Physiol., vol. 115, pp. 971–980.*

Ishida, Y. et al., "High efficiency transformation of maize (Zea mays L.) mediated by Agrobacterium tumefaciens." 1996, Nature Biotechnology, vol. 14, pp. 745–750.*

Gautier, M. et al., "Triticum aestivum puroindolines, two basic cystine–rich seed proteins: cDNA sequence analysis and developmental gene expression." 1994, Plant Molecular, vol. 25, pp. 43–57.*

Van Der Krol, A. et al., "Inhibition of Flower Pigmentation by Antisense CHS Genes: Promoter and Minimal Sequence Requirements for the Antisense Effect," *Plant Molecular Biology*, (1990) 14:457–466 Kluwer Academic Publishers.

Napoli, C., Lemieux, C. and Jorgensen, "Introduction of a Chimeric Chalone Synthase Gene into Petunia Results in Reversible Co–Suppression of Homologous Genes in trans," *The Plant Cell*, (1990) 2:279–289.

Beecher, Bettge, Smidansky and Giroux, in press, Expression of Wild–Type pinB Sequence in Transgenic Wheat Complements a Hard Phenotype, 31 pages.

Dubrieil, L., Gaborit, T., Bouchet, B. Gallant, D.J., Broekaert, W.F., Quillien, L., and Marion, D. (1998) Spatial and t emporal distribution of the major isoforms of puroindolines (puriondoline–a and puroindoline–b) and non specific lipid transfer protein (ns–LTPel) of Triticum aestivum seeds. Relationships with their in vitro antifungal properties. Plant Science Dec. 138; 121–135.

Giroux, M.J., and Morris, C.F. (1998) Wheat grain hardness results from highly conserved mutations in the friablin components puroindoline a and b. Proc. Natl. Acad. Sci. 95, 6262–6266.

Giroux, M.J., Martin, J.M., Habernicht D.K., Lanning, S., Hemphill, A., and Talbert, L. (2000) Association of Puriondoline Sequence Type and Grain Hardness in Hard Red Spring Wheat, Crop Science, 40, 370–374 (Mar. Apr. 2000).

Krishnamurthy and Giroux, 2001, Expression of wheat puroindoline genes in transgenic rice enhances grain softness, Nature Biotechnology, 19:162–166.

Morris, Craig F., in press, Puroindolines: the molecular genetic basis of wheat grain hardness, 5/6, vol. 48: 15 pages.

Prado, V.F., Lee, C.H., Zahed, L., Vekemans, M. And Nishioka, Y., Molecular Characterization of a mouse Y chromosomal repetitive sequence that detects transcripts in the testis. Cytogenet. Cell Genet. 61(2), 87–90 (1992).

Rahman, S. Jolly, C.J., Skerritt, J.H. and Wallosheck, A. Cloning of a wheat 15–kDa grain softness protein (GSP). GSP is a mixture of puroindoline–like polypeptides. Eur. J. Biochem. 223. (3) 917–925 (1994).

Tanchak, M., Schernthaner, J.P., Giband, M., and Altosarr I. Tryptophanins: isolation and molecular characterization of oat cDNA clones encoding proteins structurally related to puroindoline and wheat grain softness proteins. Plant Science 137, 173–184 (1998).

Database Genbank, NCBI, Accession No. X69912, Gautier et al. (1994).

Database Genbank, NCBI, Accession No. X69913, Gautier et al. (1995).

Database Genbank, NCBI, Accession No. X69914, Gautier et al. (1995).

(List continued on next page.)

*Primary Examiner*—David T. Fox
*Assistant Examiner*—Anne Kubelik
(74) *Attorney, Agent, or Firm*—Margaret A. Connor; John Fado

(57) ABSTRACT

This invention provides expression cassettes and vectors comprising a recombinant nucleic acid which comprises a nucleic acid sequence encoding a functional puroindoline B. This invention further provides such cassettes and vectors wherein the nucleic acid sequence encoding a functional puroindoline B is operably linked to a promoter. The invention also provides methods of producing plants with soft grain by transforming them with such expression cassettes and vectors, as well as the cells and plants produced by such methods.

8 Claims, 3 Drawing Sheets

OTHER PUBLICATIONS

Database Ganbank, NCBI, Accession No. S46515, Prado et al. (1993).

Database Genbank, NCBI, Accession No. X80378, Rahman et al. (1995).

Database Genbank, NCBI, Accession No. X80379, Rahman et al (1995).

Database Genbank, NCBI, Accession No. X80380, Rahman et al (1995).

Database Genbank, NCBI, Accession No. X80381, Rahman et al (1995).

Database Genbank, NCBI, Accession No. S72696, Rahman et al (1995).

Chevreau et al., 2001, Prov. IV IS on In Vitro Cult. & Hort. Breeding, p. 323–326.

C.F. Morris and S.P. Rose, "Wheat," In *Cereal Grain Quality*, R.J. Henry and P.S. Kettlewell (eds.), Chapman and Hall, New York, N.Y. p. 3–54 (1996).

P. Greenwell and J.D. Schofield, "A Starch Granule Protein Associated with Endosperm Softness in Wheat," *Cereal Chemistry* 63(4):379–380 (1986).

C.F. Morris, G.A. Greenblatt, A.D. Bettge and H.I. Malkawi, "Isolation and Characterization of Multiple Forms of Friabilin," *Journal of Cereal Science* 21:167–174 (1994).

C.J. Jolly, S. Rahman, A.A. Kortt, and T.J.V. Higgins, "Characterisation of the Wheat Mr 15 000 'Grain Softness Protein' and Analysis of the Relationship Between its Accumulation in the Whole Seed and Grain Softness," *Theoretical and Applied Genetics* 86:589–597 (1993).

M.–F. Gautier, M.–E. Aleman, A. Guirao, D. Marion, and P. Joudrier, "*Triticum aestivum* Puroindolines, Two Basic Cystine–rich Seed Proteins: cDNA Sequence Analysis and Developmental Gene Expression," *Plant Molecular Biology* 25:43–57 (1994).

M.J. Giroux and C.F. Morris, "A Glycine to Serine Change in Puroindoline b Is Associated with Wheat Grain Hardness and Low Levels of Starch–surface Friabilin," *Theoretical and Applied Genetics*, 95:857–864 (Oct. 1997).

J.–E. Blochet, A. Kaboulou, J.–P. Compoint, and D. Marion, "Amphiphilic Proteins from Wheat Flour: Specific Extraction, Structure and Lipid Binding Properties," *In Glutenin Proteins 1990*, W. Bushul and R. Thachuk (eds.), American Association of Cereal Chemists, St. Paul, MN. p 314–325 (1991).

J.–E. Blochet, C. Chevalier, E. Forest, E. Pebay–Peyroula, M.–F. Gautier, P. Joudrier, M. Pízolet, and D. Marion, "Complete Amino Acid Sequence of Puroindoline, a New Basic and Cystine–rich Protein with a Unique Tryptophan–rich Domain, Isolated from Wheat Endosperm by Triton X114 Phase Partitioning," *FEBS Lett* 329:336–340 (1993).

G.A. Greenblatt, A.D. Bettge, and C.F. Morris, "Relationship Between Endosperm Texture and the Occurrence of Friabilin and Bound Polar Lipids on Wheat Starch," *Cereal Chemistry* 72(2):172–176 (1995).

P.J. Wilde, D.C. Clark, and D. Marion, "The Influence of Competitive Adsorption of Lysopalmitoyl Phosphatidylcholine on the Functional Properties of Puroindoline, a Lipid Binding Protein Isolated from Wheat Flour,"*Journal of the Science of Food and Agriculture* 41:1570–1576 (1993).

* cited by examiner

MODIFICATION OF CEREAL GRAIN HARDNESS VIA EXPRESSION OF PUROINDOLINE PROTEIN

CROSS-REFERENCE TO RELATED APPLICATIONS

Not Applicable.

FEDERALLY SPONSORED RESEARCH AND DEVELOPMENT

Not Applicable.

BACKGROUND OF THE INVENTION

Cereals, including wheat (*Triticum aestivum* L. em Thell.), are the most important food crops in the world. In addition to use in feed for livestock, the grain from cereals are milled into flour in almost every culture. Wheat flour is found extensively throughout the world but particularly in Europe and North America, rice flour is used extensively in Asia, sorghum flour in Africa, and corn flour (or meal) in the Americas.

The grain of cereal plants varies between species and within species of cereal plants. Grain texture refers to the texture of the kernel (caryopsis), that is, whether endosperm is physically hard or soft. Typically, rice, sorghum, barley and maize are hard textured grains while oat, rye and triticale are soft. Nearly all of the world production and trade in wheat (approximately 550 and 100 mmt annually, respectively) is identified as being either soft or hard. Generally speaking, hard wheat is used for bread whereas soft wheat is used for cookies, cakes and pastries (Morris & Rose, *Cereal Grain Quality*, Chapman & Hall, New York, N.Y., pp. 3–54 (1996)). The very hard durum wheat (*T. turgidum*) is generally used in pasta.

In addition to differences in taste and water absorption, grain texture dictates milling techniques. Typically, the harder the grain, the more energy is required for milling, the greater the starch damage during the milling process, and the larger the milled particle size.

A 15 kDa marker protein for grain softness, termed friabilin, is present on the surface of water-washed starch from soft wheats in high amounts, on hard wheat starch in small amounts, and absent on durum wheat starch (Greenwell & Schofield, *Cereal Chem.* 63:379–380 (1986)). N-terminal sequence analysis of friabilin indicates a mixture of two or more discrete polypeptides (Morris, et al., *J. Cereal Sci.* 21:167–174 (1994); and Jolly, et al., *Theor. Appl. Genet.* 86:589–597 (1993)). The two major component polypeptides have been found to be identical to the two lipid binding proteins termed puroindolines (Gautier, et al., *Plant Molec. Biol.* 25:43–57 (1994)), puroindoline A (puro A) and puroindoline B (puro B), respectively. The transcripts of puro A and puro B, are controlled by chromosome 5D (Giroux & Morris, *Theor. Appl. Genet.* 95:857–864 (1997)).

Puro A and puro B are unique among plant proteins because of their tryptophan-rich, hydrophobic domains, which have affinity for binding lipids (Blochet, et al., *Gluten Proteins* 1990, Bushuk & Tkachuk (eds), American Association of Cereal Chemists, St. Paul, Minn., pp. 314–325 (1991); and Wilde, et al., *Agric. Res.* 20:971 (1993)). The association of friabilin (puro A and puro B) with the surface of the starch granule is apparently mediated by polar lipids. In fact, the occurrence of membrane structural lipids, glyco- and phospho-lipids, with the surface of water washed starch follows that of friabilin (Greenblatt, et al., *Cereal Chem.* 72:172–176 (1995)): high amounts are present on soft wheat starch, low amounts on hard wheat starch, and none on durum.

There exists a need to modify the texture of grain in cereal plants with more certainty than is available by hybrid crossing. With hybrid crossing, there is the possibility that the parent plants will be reproductively incompatible. There also is the very real possibility that large amounts of water, fertilizer and acreage will be necessary to produce one hybrid plant. By creating transgenic plants with nucleic acid sequences that alter the texture of grain, these problems can be averted. This invention meets this and other needs

BRIEF SUMMARY OF THE INVENTION

This invention provides for the identification of puroindoline A and puroindoline B as the major components of grain softness in wheat (*Triticum aestivum*). This invention also provides for methods of introducing puroindoline genes and puroindoline homologs into wheat and other cereal plants to modify grain texture.

In a preferred embodiment, a method of producing a transgenic plant with softer textured grain from at least one parent plant with hard textured grain is provided. The method comprises the steps of introducing a nucleic acid sequence which hybridizes under stringent conditions to a nucleic acid sequence selected from the group consisting of SEQ ID NO:1 and SEQ ID NO:3 and operably encodes a puroindoline protein into a cell from the parent plant, and generating a plant from the cell containing the nucleic acid sequence. In a more preferred embodiment, the plant is selected from the group consisting of durum wheat, sorghum, rice, barley and maize. In a most preferred embodiment, the plant is maize. In a preferred embodiment, the introduction of the nucleic acid is mediated by Agrobacterium infection. Also in this embodiment, it is preferred that the puroindoline protein is selected from the group consisting of puroindoline A and puroindoline B.

Another embodiment of this invention provides for a method of producing a transgenic plant with harder textured grain, wherein the plant is derived from at least one parent plant with soft textured grain. The method comprises the steps of introducing a nucleic acid sequence which prevents expression of a puroindoline protein or homolog into a cell from the parent plant and generating the plant from the cell. In a particularly preferred aspect of this embodiment, the plant is selected from the group consisting of wheat, rye, triticale, and oat.

In another preferred aspect of this embodiment the nucleic acid sequence is introduced into a cell and prevents expression of puroindoline A or puroindoline B by operably encoding a ribozyme. In a more preferred embodiment, the nucleic acid sequence operably encodes an antisense nucleic acid which hybridizes under stringent conditions to a nucleic acid sequence complementary to SEQ ID NO:1 or SEQ ID NO:3. Depending on the cereal plant, the nucleic acid can operably encode a transposon. In another aspect of this invention, the nucleic acid sequence is introduced into the plant by Agrobacterium infection.

In yet another embodiment of this invention, a method of producing a transgenic plant with harder textured grain is provided, wherein the plant is derived from at least one parent plant with soft textured grain. The method comprises the steps of introducing a nucleic acid sequence into a cell from the parent plant, wherein the nucleic acid sequence hybridizes under stringent conditions to a nucleic acid as shown in SEQ ID NO:5 and generating the plant from the cell. In a more preferred embodiment, the plant is selected from the group consisting of wheat, rye, triticale and oat. In a preferred aspect of this embodiment, the nucleic acid sequence is introduced into the plant by Agrobacterium infection.

In still another embodiment, a transgenic plant with soft textured grain is provided. The plant is derived from at least one parent plant which has hard textured grain. The plant comprises a nucleic acid sequence which operably encodes a puroindoline protein, wherein the nucleic acid sequence hybridizes under stringent conditions to a nucleic acid sequence selected from the group consisting of SEQ ID NO:1 and SEQ ID NO:3. In a more preferred embodiment, the plant is selected from the group consisting of durum wheat, sorghum, rice, barley and maize. In a particularly preferred embodiment, the plant is maize.

In this embodiment, the puroindoline nucleic acid sequence is introduced into the plant by transformation and the puroindoline protein is selected from the group consisting of puroindoline A and puroindoline B. In a particularly preferred embodiment, transformation is by Agrobacterium infection.

In still another embodiment of this invention, a transgenic plant with harder textured grain is provided. The plant is derived from at least one parent having soft textured grain and comprises a nucleic acid sequence which prevents expression of puroindoline proteins. In a particularly preferred aspect of this embodiment, the progeny plant is selected from the group consisting of wheat, rye, triticale and oat.

In a preferred aspect of this embodiment, the nucleic acid sequence is introduced into a wheat cell and prevents expression of puroindoline A or puroindoline B by operably encoding a ribozyme or a transposon. However, it is preferred that the nucleic acid sequence operably encodes an antisense nucleic acid which hybridizes to a nucleic acid sequence which is complementary to SEQ ID NO:1 or SEQ ID NO:3. In a particularly preferred embodiment, the nucleic acid sequence is introduced into the plant by Agrobacterium infection.

In yet another embodiment, this invention provides for a transgenic plant with hard grain derived from at least one parent having soft grain. The plant comprises a nucleic acid sequence which hybridizes under stringent conditions to a nucleic acid sequence selected from the group consisting of SEQ ID NO:5.

BRIEF DESCRIPTION OF THE SEQUENCES

SEQ ID NO:1 is the cDNA sequence of puroindoline A.

SEQ ID NO:2 shows the amino acid sequence encoded by SEQ ID NO:1.

SEQ ID NO:3 is the cDNA sequence of puroindoline B.

SEQ ID NO:4 shows the amino acid sequence encoded by SEQ ID NO:3.

SEQ ID NO:5 is the cDNA sequence of serine substituted puroindoline B.

SEQ ID NO:6 shows the amino acid sequence encoded by SEQ ID NO:5.

SEQ ID NO:7 is a sense strand primer for puroindoline A.

SEQ ID NO:8 is an antisense strand primer for puroindoline A.

SEQ ID NO:9 is a sense strand primer for puroindoline B.

SEQ ID NO:10 is an antisense strand for puroindoline B.

SEQ ID NO:11 is an anti sense strand for serine substituted puroindoline B.

SEQ ID NO:12 is a GSP1 sense strand.

SEQ ID NO:13 is a GSP1 antisense strand.

DEFINITIONS

Figure 1:
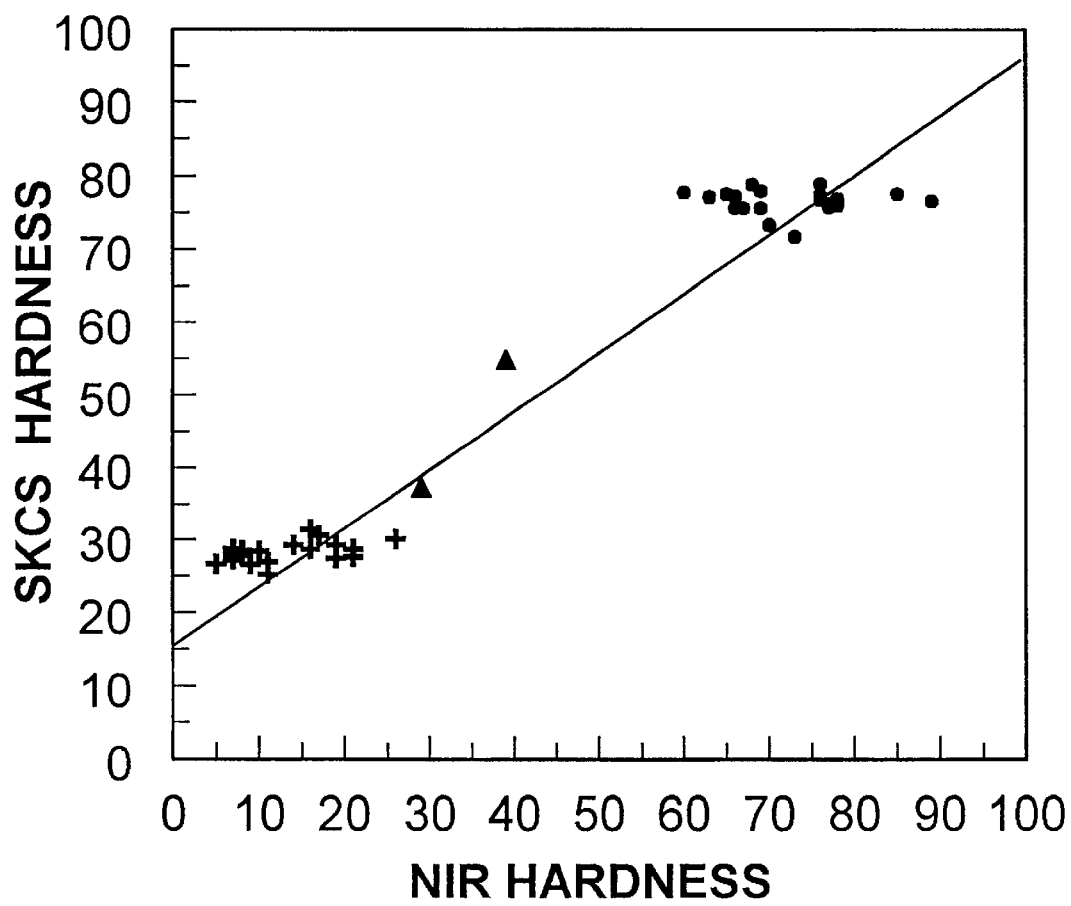
FIG. 1 is a graph showing there is no evidence for recombination between puro A and grain softness. Phenotypic grain hardness of 44 Falcon/Heron hard/soft NILs (Near Isogenic Lines) as measured by Single Kernel Characterization System (SKCS) vs. NIR hardness. Presence or absence of puro A is as shown (+ puro A present; ● puro A absent; ▲ NILs consisting of physical mixtures of seeds containing and lacking puro A).
Figure 2A:
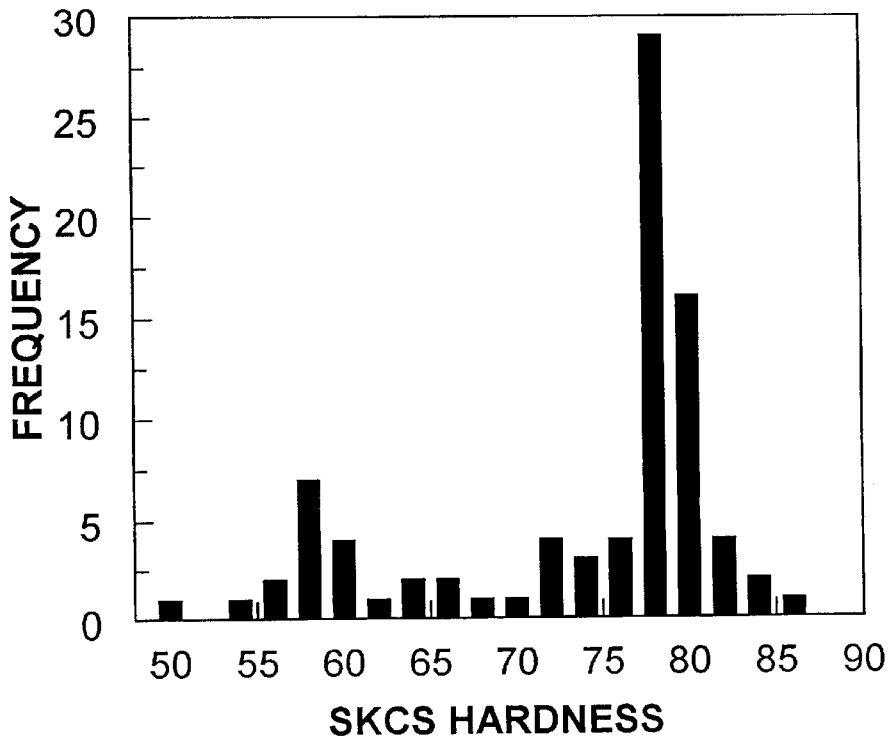
FIG. 2A is a frequency distribution histogram of SKCS single-kernel hardness readings of the 83 hard/soft chromosome 5D recombinants and parents, "Chinese Spring" (CS) and "Chinese Spring" substituted Cheyenne 5D (CS (CNN5D)). Readings are the average of two replications for each of two locations. Parental values were 60 and 79, CS and CS(CNN5D), respectively.
Figure 2B:
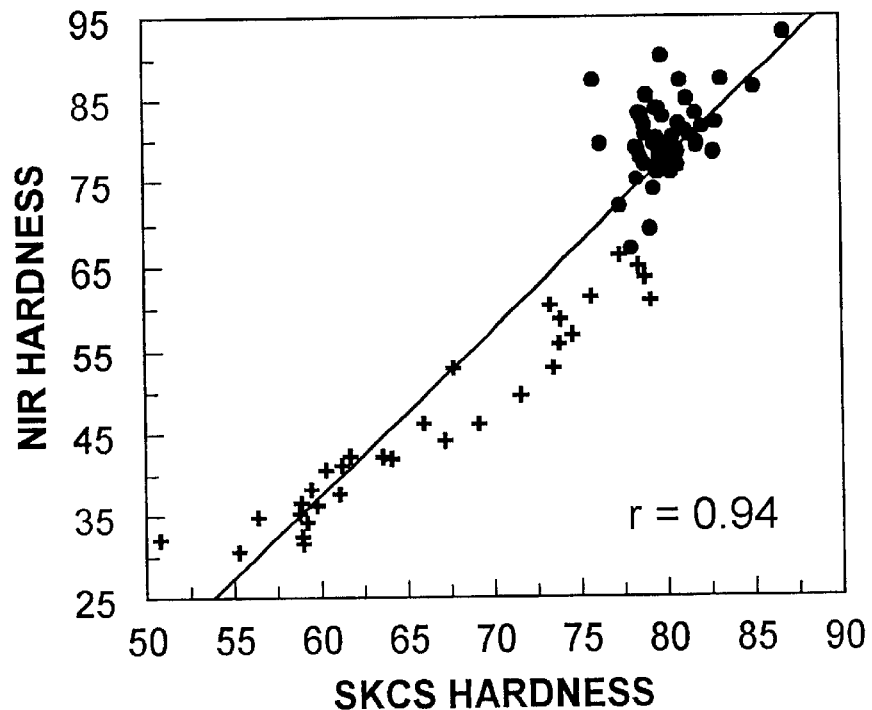
FIG. 2B graphically reflects the SKCS single kernel versus NIR hardness readings. Recombinants are classified according to puroindoline b sequence type where (+) denotes the glycine sequence type of the soft parent, "Chinese Spring," and (●) denotes the serine sequence type of the hard parent "Chinese Spring" substituted Cheyenne 5D.
Figure 3:
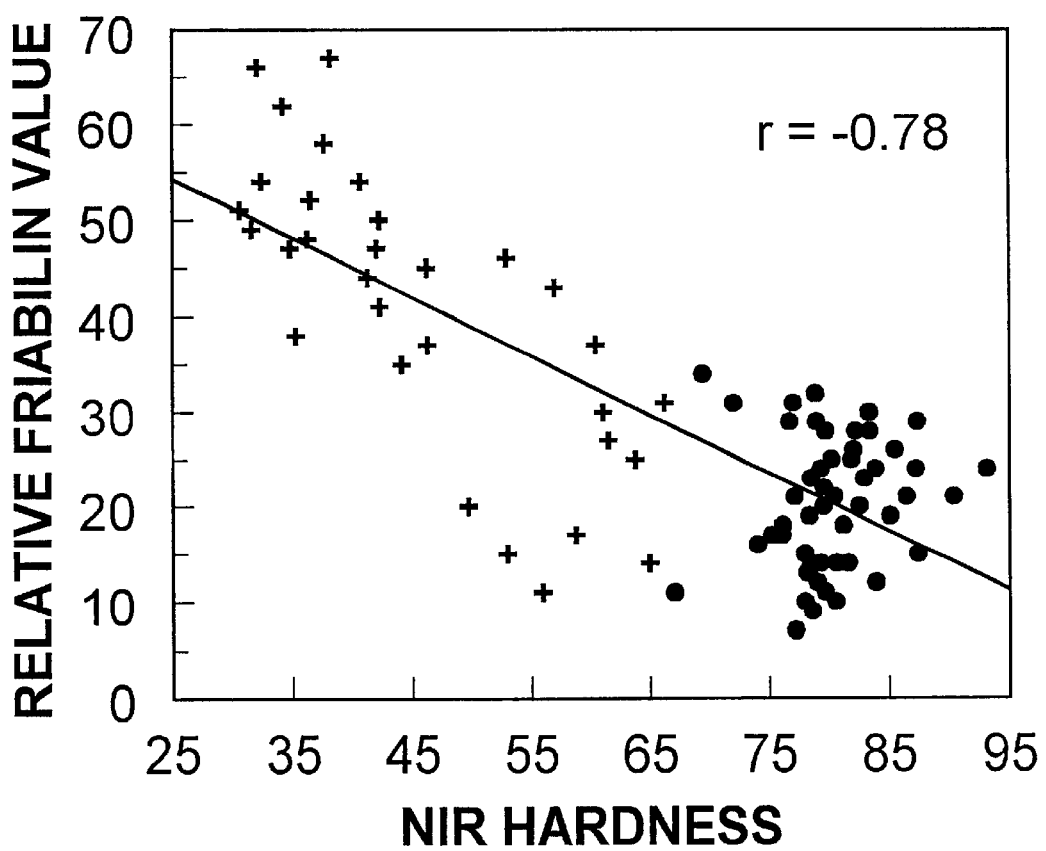
FIG. 3 shows the relative amount of starch surface friabilin as a percentage of the soft parent "Chinese Spring" for soft/hard recombinants versus NIR hardness. Recombinants are classified according to puroindoline b sequence type where (+) denotes the glycine sequence type of the soft parent, "Chinese Spring," and (●) denotes the serine sequence type of the hard parent "Chinese Spring" substituted Cheyenne 5D.

Unless defined otherwise, all technical and scientific terms used herein have the meaning commonly understood by a person skilled in the art to which this invention belongs. The following references provide one of skill with a general definition of many of the terms used in this invention: Singleton, et al., *Dictionary of Microbiology and Molecular biology* (2d ed. 1994); *The Cambridge Dictionary of Science and Technology* (Walker ed., 1988); *The Glossary of Genetics*, 5th Ed., Rieger, R., et al.(eds.), Springer Verlag (1991); and Hale & Marham, *The Harper Collins Dictionary of biology* (1991). As used herein, the following terms have the meanings ascribed to them unless specified otherwise.

The term "cell" can refer to any cell from a plant, including but not limited to, somatic cells, gametes or embryos. "Embryo" refers to a sporophytic plant before the start of germination. Embryos can be formed by fertilization of gametes by sexual crossing or by selfing. A "sexual cross" is pollination of one plant by another. "Selfing" is the production of seed by self-pollinization, i.e., pollen and ovule are from the same plant. The term "backcrossing" refers to crossing a $F_1$ hybrid plant to one of its parents. Typically, backcrossing is used to transfer genes which confer a simply inherited, highly heritable trait into an inbred line. The inbred line is termed the recurrent parent. The source of the desired trait is the donor parent. After the donor and the recurrent parents have been sexually crossed, $F_1$ hybrid plants which possess the desired trait of the donor parent are selected and repeatedly crossed (i.e., backcrossed) to the recurrent parent or inbred line.

Embryos can also be formed by "embryo somatogenesis" and "cloning." Somatic embryogenesis is the direct or indirect production of embryos from cells, tissues and organs of plants. Indirect somatic embryogenesis is characterized by growth of a callus and the formation of embryos on the surface of the callus. Direct somatic embryogenesis is the formation of an asexual embryo from a single cell or group of cells on an explant tissue without an intervening callus phase. Because abnormal plants tend to be derived from a callus, direct somatic embryogenesis is preferred.

The phrase "grain texture" refers to the main basis of classification of wheat grown for market. The common term, "grain" is the endosperm present in the ovules of a plant. In wheat, texture of the grain or endosperm is distinguished by expression of the Hardness gene. However, all cereal grains can be classified on the basis of grain texture. In Sorghum and maize, softer endosperm results from mutations in genes such as opaque-2 and floury-2. However, expression of these mutant genes is recessive and leads to other, deleterious phenotypes such as greater susceptibility to mechanical and insect damage.

"Softer textured grain" refers to grain produced by a progeny or transgenic plant that is 10 units less than the grain produced by at least one of the plant's parent as measured by the Perten SKCS 4100 (Perten Instruments, Reno, Nev.); by near-infra red reflectance spectroscopy (NIR) as described in Method 39–70 (*Approved Methods of the American Association of Cereal Chemists, 9th Ed.*, American Association of Cereal Chemists, St. Paul, Minn. (1995); or by equivalent technology. In a more preferred embodiment, the grain of the progeny or transgenic plant is at least 20 units lower than the grain of at least one of the parents. In a most preferred embodiment, the grain of the progeny or transgenic plant is at least 40 units lower than the grain of the parent. However, because grain hardness is a quantitative trait, one of skill will realize that hardness of grain is determined in part by the environment in which the progeny or transgenic plant and parent plants are grown.

"Harder textured grain" refers to grain produced by a progeny plant that is at least 10 units greater than the grain produced by at least one of the progeny plant's parent as measured by the techniques described above. In a more preferred embodiment, the grain of the progeny or transgenic plant is at least 20 units greater than the grain of at least one of the parents. In a most preferred embodiment, the grain of the progeny or transgenic plant is at least 40 units greater than the grain of the parent.

The phrase "hybridizes under stringent conditions" refers to the formation of a double-stranded duplex from two single-stranded nucleic acids. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid. An extensive guide to the hybridization of nucleic acids is found in Tijssen, *Laboratory Techniques in Biochemistry and Molecular biology—Hybridization with Nucleic Acid Probes Parts I and II*, Elsevier, New York, (1993). Generally, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Highly stringent conditions are selected to be equal to the $T_m$ point for a particular probe. Sometimes the term "$T_d$" is used to define the temperature at which at least half of the probe dissociates from a perfectly matched target nucleic acid. In any case, a variety of estimation techniques for estimating the $T_m$ or $T_d$ are available, and generally described in Tijssen, id. Typically, G-C base pairs in a duplex are estimated to contribute about 3° C. to the $T_m$, while A-T base pairs are estimated to contribute about 2° C., up to a theoretical maximum of about 80–100° C. However, more sophisticated models of $T_M$ and $T_d$ are available and appropriate in which G-C stacking interactions, solvent effects, the desired assay temperature and the like are taken into account. In one example, PCR primers are designed to have a dissociation temperature ($T_d$) of approximately 60° C., using the formula: $T_d=(((((3\times\#GC)+(2\times\#AT))\times37)-562)/\#bp)-5$; where #GC, #AT, and #bp are number of guanine-cytosine base pairs, the number of adenine-thymine base pairs, and the number of total base pairs, respectively, involved in the annealing of the primer to the template DNA.

An example of stringent hybridization conditions for hybridization of complementary nucleic acids that have more than 100 complementary residues on a filter in a Southern or northern blot is 50% fornalin with 1 mg of heparin at 42° C., with the hybridization being carried out overnight. An example of stringent wash conditions for a Southern blot of such nucleic acids is a 0.2×SSC wash at 65° C. for 15 minutes (see, Sambrook, et al., *Molecular Cloning—A Laboratory Manual* (2nd ed.) Vol. 1–3, Cold Spring Harbor Laboratory, Cold Spring Harbor Press, NY, 1989 (Sambrook) for a description of SSC buffer). Often the high stringency wash is preceded by a low stringency wash to remove background probe signal. An example low stringency wash is 2×SSC at 40° C. for 15 minutes.

In general, a signal to noise ratio of 2× (or higher) than that observed for an unrelated probe in the particular hybridization assay indicates detection of a specific hybridization. For highly specific hybridization strategies such as allele-specific hybridization, an allele-specific probe is usually hybridized to a marker nucleic acid (e.g., a genomic nucleic acid, or the like) comprising a polymorphic nucleotide under highly stringent conditions.

The phrase "introducing a nucleic acid sequence" refers to introducing nucleic acid sequences by recombinant means, including but not limited to, Agrobacterium-mediated transformation, biolistic methods, electroporation, in planta techniques, and the like. The term "nucleic acids" is synonymous with DNA, RNA, and polynucleotides. Such a plant containing the nucleic acid sequences is referred to here as an $R_1$ generation plant. $R_1$ plants may also arise from cloning, sexual crossing or selfing of plants into which the nucleic acids have been introduced.

"Transgenic plants" are plants into which the nucleic acid has been introduced through recombinant techniques, e.g., nucleic acid-containing vectors. A "vector" is a nucleic acid composition which can transduce, transform or infect a cell, thereby causing the cell to express vector-encoded nucleic acids and, optionally, proteins other than those native to the cell, or in a manner not native to the cell. A vector includes a nucleic acid (ordinarily RNA or DNA) to be expressed by the cell. A vector optionally includes materials to aid in achieving entry of the nucleic acid into the cell, such as a retroviral particle, liposome, protein coating or the like. Vectors contain nucleic acid sequences which allow their propagation and selection in bacteria or other non-plant organisms. For a description of vectors and molecular biology techniques, see *Current Protocols in Molecular biology*, Ausubel, et al., (eds.), Current Protocols, a joint venture between Greene Publishing Associates, Inc. and John Wiley & Sons, Inc., (through and including the 1998 Supplement) (Ausubel).

The phrase "expression cassette" refers to a nucleic acid sequence within a vector which is to be transcribed, and a promoter to direct the transcription. A "promoter" is an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. The promoter can either be homologous, i.e., occurring naturally to direct the expression of the desired nucleic acid or heterologous, i.e., occurring naturally to direct the expression of a nucleic acid derived from a gene other than the desired nucleic acid. Fusion genes with heterologous promoter sequences are desirable, e.g., for regulating expression of encoded proteins. A "constitutive" promoter is a promoter that is active in a selected organism under most environmental and developmental conditions. An "inducible" promoter is a promoter that is under environmental or developmental regulation in a selected organism.

The phrase "operably encodes" refers to the functional linkage between a promoter and a second nucleic acid sequence, wherein the promoter sequence initiates transcription of RNA corresponding to the second sequence.

The phrase "prevents expression of a puroindoline protein" refers to inhibition of puroindoline protein synthesis in the cells of a plant. Inhibition can be either at the transcription level, i.e., synthesis of corresponding mRNA, or the translation level, i.e., synthesis of protein. For purposes of this invention, preventing expression of puroindoline proteins is accomplished through the introduction of nucleic acid sequences which suppress synthesis of mRNA or protein. The nucleic acid may encode mRNA transcripts that inhibit expression of puroindoline genes and provide a harder-textured grain. For example, anti-sense RNA inhibition of gene expression has been shown; see, e.g., Sheehy, et al., *Proc. Nat'l Acad. Sci. USA* 85:8805–8809 (1988), and U.S. Pat. No. 4,801,340. Sense suppression has also been used to modulate expression of endogenous genes, see, Napoli, et al., *The Plant Cell* 2:279–289 (1990), and U.S. Pat. No. 5,034,323.

Antisense technology comprises cloning a nucleic acid segment from the desired puroindoline gene and operably linking it to a promoter such that the antisense (or complementary) strand of RNA will be transcribed. The construct is then transformed into plants and the antisense strand of RNA is produced.

The nucleic acid segment to be introduced generally will be substantially identical to at least a portion of the puroindoline gene or genes to be suppressed. The sequence, however, need not be perfectly identical to inhibit expression. The introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about 2000 nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit gene expression. It is possible to design ribozymes that specifically pair with virtually any target RNA and cleave the phosphodiester backbone at a specific location, thereby functionally inactivating the target RNA. In carrying out this cleavage, it is a true enzyme. The inclusion of ribozyme sequences within antisense RNAs confers RNA-cleaving activity upon them, thereby increasing the activity of the constructs. A general design and use of target RNA-specific ribozymes is described in Haseloff, et al., *Nature* 334:585–591 (1988).

"Transposon" refers to sequences of DNA that have the ability to move or to jump to new locations within a genome. Two components are required for transposition: the transposase enzyme which catalyzes transposition and the nucleotide sequences present at the end of the transposon upon which the enzyme acts. Transposons are both autonomous and non-autonomous. Autonomous transposons are those which are capable of both transposing and catalyzing the transposition of non-autonomous elements. Examples of autonomous transposons are the Ac elements and Spm transposons isolated from maize, all of which have been cloned and are well-described in the art. See, for example, U.S. Pat. No. 4,732,856 and Gierl, et al., *Plant Mol. Biol.* 13:261–266 (1989).

Autonomous transposons comprise sequences for transposase and sequences that are recognized by the transposase enzyme at the ends of the transposon (the "Ds element"). The sequences for transposase (or the transposase gene) are active independent of the end sequences, i.e., if the end sequences are eliminated, the activity of the transposase gene is preserved and the enzyme encoding element may thus be used in conjunction with a non-autonomous or Ds element to trigger transposition of the Ds element. The transposase gene is evident in the Ts101 and Ts105 elements.

Only the DNA sequences present at the ends of a non-autonomous element are required for it to be transpositionally active in the presence of the transposase gene. These ends are referred to herein as the "transposon ends" or the "Ds element." See, for example, Coupland, et al., *Proc. Nat'l Acad. Sci. USA* 86:9385 (1989), which describes the sequences necessary for transposition. The DNA sequences internal to the transposon ends are non-essential and can be comprised of sequences from virtually any source, including exogenous mutated puroindoline nucleic acid sequences. Thus, when the transposon inserts into a genome, the correct nucleic acid sequence is excised and replaced with the mutated sequence. Because of mutations within the sequence, the puroindoline protein produced by the plant will contain a mutation or will be truncated if a stop codon is inserted.

The term "progeny" refers to the descendants of a particular plant (self-cross) or pair of plants (crossed or backcrossed). The descendants can be of the $F_1$, the $F_2$, or any subsequent generation. Typically, the parents are the pollen donor and the ovule donor which are crossed to make the progeny plant of this invention. Parents also refer to $F_1$ parents of a hybrid plant of this invention (the $F_2$ plants). Finally, parents refer to a recurrent parent which is backcrossed to hybrid plants of this invention to produce another hybrid plant of this invention.

The phrase "producing a transgenic plant" refers to producing a plant of this invention. The plant is generated through recombinant techniques, i.e., cloning, somatic embryogenesis or any other technique used by those of skill to produce plants.

The common names of plants used throughout this disclosure refer to varieties of plants of the following genera:

| Common Name | Genera |
| --- | --- |
| Wheat (soft, hard and durum varieties) | Triticum |
| Sorghum | Sorghum |
| Rice | Oryza |
| Barley | Hordeum |
| Maize or corn | Zea |
| Rye | Secale |
| Triticale | Triticale |
| Oat | Avena |

The phrase "puroindoline protein" refers to a class of proteins, including but not limited to, "puroindoline A" or "puro A" and "puroindoline B" or "puro B." PuroA and puro B are have tryptophan-rich hydrophobic domains which have affinity for binding lipids (Blochet, et al., *Gluten Proteins* 1990, Bushak & Tkachuk (eds.), American Association of Cereal Chemists, St. Paul, Minn. (1991); and Wilde, et al., *Agric. Res.* 20:971 (1993)). In addition to the puroindoline proteins found in wheat, puroindoline proteins, for purposes of this invention, also refer to puroindoline homologs. Homologs refers to proteins having a homologous function, i.e., affecting the texture of grain, for example, avenin from oat. Homologs also refer to nucleic acid sequence or amino acid sequence homologs.

"Nucleic acid sequence homologs" refers to deoxyribonucleotides or ribonucleotides and polymers thereof in either single- or double-stranded form containing known analogs of natural nucleotides, which have similar binding properties as the reference nucleic acid and are metabolized in a manner similar to naturally occurring nucleotides.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer, et al., *Nucleic Acid Res.* 19:5081 (1991); Ohtsuka, et al., *J. Biol. Chem.* 260:2605–2608 (1985); and Rossolini, et al., *Mol. Cell. Probes* 8:91–98 (1994)). The term nucleic acid is used interchangeably with gene, cDNA, and mRNA encoded by a gene.

The term "amino acid sequence homolog" refers to a protein with a similar amino acid sequence. One of skill will realize that the critical amino acid sequence is within a functional domain of a protein. Thus, it may be possible for a homologous protein to have less than 40% homology over the length of the amino acid sequence but greater than 90% homology in one functional domain. In addition to naturally occurring amino acids, homologs also encompass proteins in which one or more amino acid residue is an artificial chemical analog of a corresponding naturally occurring amino acid, as well as to naturally occurring proteins.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence that alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, *Proteins* (1984)).

The term "transformation" refers to the introduction of nucleic acid into plant cells, either in culture or in the organs of a plant by a variety of techniques used by molecular biologists. For example, nucleic acids can be introduced directly into the genomic DNA of the plant cell using techniques such as electroporation and microinjection of plant cell protoplasts, or the DNA constructs can be introduced directly to plant cells using ballistic methods, such as DNA particle bombardment. Alternatively, the DNA constructs are combined with suitable T-DNA flanking regions and introduced into a conventional *Agrobacterium tumefaciens* host vector. The virulence functions of the *Agrobacterium tumefaciens* host directs the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski, et al., *EMBO J.* 3:2717 (1984). Electroporation techniques are described in Fromm, et al., *Proc. Nat'l. Acad. Sci. USA* 82:5824 (1985). Ballistic transformation techniques are described in Klein, et al., *Nature* 327:70–73 (1987).

*Agrobacterium tumefaciens*-mediated transformation techniques, including disarming and use of binary vectors, are also well described in the scientific literature. See, for example Horsch, et al., *Science* 233:496–498 (1984), and Fraley, et al., *Proc. Nat'l. Acad. Sci. USA* 80:4803 (1983).

DETAILED DESCRIPTION OF THE INVENTION

This invention relates to plant puroindoline genes, in particular, wheat puroindoline A and puroindoline B genes. Nucleic acid sequences from puroindoline genes can be used to modify the texture of grain in both transgenic and progeny cereal plants. The puroindoline genes of this invention can be expressed in cereal species commonly used for production of flour, food stuffs and/or feed, e.g., wheat, rye, oats, maize and the like. By adding puroindoline genes to the genome of a cereal plant, the grain of the plant becomes softer textured than the grain of its parent. By blocking expression of puroindoline genes, the grain becomes harder than the grain of a cereal plant's parent. In addition, because of the quantitative nature of grain texture, introducing mutant forms of the puroindoline genes effects modifications in grain texture of cereal plants.

Generally, the nomenclature and the laboratory procedures in plant maintenance and breeding as well as recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook, et al., *Molecular Cloning—A Laboratory Manual*, Cold Spring Harbor Laboratory, Cold Spring Harbor, N.Y., (1989) and Dodds & Roberts, *Experiments in Plant Tissue Culture*, 3rd Ed., Cambridge University Press (1995).

I. PUROINDOLINE PROTEINS AND GENES

The difference in wheat grain texture results from the expression of one major gene, designated Hardness (Ha) (Symes, *Aust. J. Agric. Res.* 16:113–123 (1965); and Baker, *Crop Sci.* 17:960–962 (1977)) located on the short arm of chromosome 5D (Mattern, et al., *Proceedings of the 4th International Wheat Genetics Symposium*, University of Missouri, Columbia, Mo., pp. 703–707 (1973); and Law, et al., *Seed Protein Improvement by Nuclear Techniques*, International Atomic Energy Agency, Vienna, Austria. pp. 483–502 (1978)).

The presence of a single major gene is contrary to the allohexaploid nature of wheat (*T. aestivum*) (2n=6x=42 chromosomes; genomes AABBDD) since most genes exist in triplicated homoeologous sets, one from each genome. Alleles of the hardness gene are present on the 5A and 5B chromosomes of hexaploid wheat but are not expressed. For this reason, durum wheats (*T. turgidum* L. var. *durum*) (2n=4x=28 chromosomes; genomes AABB) which lack the D genome are generally harder textured than hard hexaploid wheat.

The puroindoline proteins of wheat are cysteine and tryptophan-rich lipid binding proteins found in the endosperm of seed. Mature puroindoline A and B are 148 amino acids in length with molecular weights of 16,792 and 16,387 Daltons, respectively (Gautier, et al., *Plant Mol. Biol.* 25:43 (1994). They share 55% amino acid homology and are very basic, with a pI greater than 10 for both proteins.

Studies have shown that both puroindoline A and puroindoline B must be expressed to confer softness to wheat. A glycine to serine change (Gly-46 to Ser-46) in the tryptophan-rich domain of puro B has been reported in two hard wheat varieties (Giroux & Morris, *Theor. Appl. Genet.* 95:857–864 (1997)). See, SEQ ID NO:5. This sequence change was inseparably linked to grain hardness and could lessen the strength of lipid binding due to the inherent decrease in hydrophobicity of a glycine to serine change (Thorgeirsson, et al., *Biochem.* 35:1803–1809 (1996)). The complete linkage between this mutation in puro B and hard grain texture among 83 chromosome 5D recombinant substitution lines suggested that this protein is involved in the control of grain softness (Giroux & Morris, *Theor. Appl. Genet.* 95:857–864 (1997)). The change present in puro B was identical in two different hard textured varieties and absent in two soft textured reference varieties. This change could have simply represented a tight linkage between the friabilin component puro B and the Hardness gene.

Any isolated puroindoline or puroindoline homolog gene can be used in the present invention. The particular polynucleotide sequence used is not a critical feature of the invention, so long as the desired alteration in grain texture is achieved. As noted above, both puroindolines are encoded at the Ha locus. In hexaploid wheat, the group 5 chromosomes are designated 5A, 5B and 5D. The Ha locus has been found on the 5D chromosome. Because tetraploid durum wheat (*Triticum turgidum*) is missing the D group of chromosomes, the Ha locus is absent and durum wheat is universally hard.

Wheat puroindoline genes have been cloned and are described in the literature. For instance, cDNA of both puroindoline A and puroindoline B have been isolated and sequenced from a *Triticum aestivum* mid-maturation seed cDNA library (Gautier, et al., *Plant Mol. Biol.* 25:43 (1994)).

The isolation of other puroindoline or puroindoline homolog genes, including non-functional sequence homologs, may be accomplished by a number of techniques. For instance, oligonucleotide probes based on the sequences disclosed in the prior art can be used to isolate the desired gene from a cDNA or genomic DNA library. To construct genomic libraries, large segments of genomic DNA are generated by random fragmentation, e.g., using restriction endonucleases, and are ligated with vector DNA to form concatamers that can be packaged into the appropriate vector. To prepare a cDNA library, mRNA is isolated from endosperm and a cDNA library which contains the puroindoline gene transcript is prepared from the mRNA.

Alternatively, the nucleic acids of interest can be amplified from nucleic acid samples using amplification techniques. For instance, polymerase chain reaction (PCR) technology to amplify the sequences of the puroindolines and related genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see, *PCR Protocols: A Guide to Methods and Applications*, Innis, et al.(eds.), Academic Press, San Diego (1990).

Polynucleotides may also be synthesized by well-known techniques as described in the technical literature. See, e.g., Carruthers, et al., *Cold Spring Harbor Symp. Quant. Biol.* 47:411–418 (1982), and Adams, et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Isolated sequences prepared as described herein can then be used to modify puroindoline gene expression and therefore grain texture in plants. One of skill will recognize that the nucleic acid encoding a functional puroindoline protein need not have a sequence identical to the exemplified genes disclosed here. Thus, genes encoding chimeric puroindoline polypeptides can be used in the present invention.

As noted above, puroindoline polypeptides, like other proteins, have different domains which perform different functions. Thus, the puroindoline gene sequences need not be full length, so long as the desired functional domains of the protein is expressed. Chimeric puroindoline polypeptides can be readily designed utilizing various recombinant DNA techniques well known to those skilled in the art. For example, the chains can vary from the naturally occurring sequence at the primary structure level by amino acid substitutions, additions, deletions, and the like. In particular, cysteine residues may be added, deleted or moved within the polypeptide to achieve a modified puroindoline polypeptide with desired properties. Chimeric polypeptides may also be produced by fusing coding sequences from two or more puroindoline genes. All of these modifications can be used in a number of combinations to produce the final modified protein chain.

II. PREPARATION OF RECOMBINANT CONSTRUCTS

In one embodiment of this invention, to modify grain texture in plants, recombinant DNA vectors which contain isolated puroindoline sequences and are suitable for transformation of plant cells are prepared. A DNA sequence coding for the desired puroindoline polypeptide, for example a cDNA or a genomic sequence encoding a full length protein, is conveniently used to construct a recombinant expression cassette which can be introduced into the desired plant. An expression cassette will typically comprise the puroindoline nucleic acid sequence operably linked to a promoter sequence and other transcriptional and translational initiation regulatory sequences which will direct the transcription of the sequence from the puroindoline gene or puroindoline antisense in the intended tissues (e.g., endosperm) of the transformed plant.

For example, a constitutive plant promoter fragment may be employed which will direct expression of the puroindoline proteins in all tissues of a plant. Such promoters are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may be under environmental control. Such promoters are referred to here as "inducible" promoters. Examples of environmental conditions that may effect transcription by inducible promoters include pathogen attack, anaerobic conditions, or the presence of light.

Typically, the promoters used in the constructs of the invention will be "tissue-specific" and are under developmental control such that the desired gene is expressed only in certain tissues, such as endosperm. Promoters that direct expression in seeds, particularly the endosperm are particularly preferred. Examples of such promoters include the promoter from genes encoding seed storage proteins, such as napin, cruciferin, phaseolin, and the like (see, U.S. Pat. No. 5,420,034). Other promoters suitable for expressing puroindoline genes in cereals include promoters from genes encoding gliadins, cereal prolamines (e.g., zein, hordein, secalin, and avenin) and starch biosynthetic enzymes.

The endogenous promoters from puroindoline genes are particularly useful for directing expression of puroindoline genes to the seed, particularly the endosperm. These seed-specific promoters can also be used to direct expression of heterologous structural genes. Thus, the promoters can be used in recombinant expression cassettes to drive expression of any gene whose expression in seeds is desirable. Examples include genes encoding proteins useful in increasing the nutritional value of seeds (e.g., genes encoding proteins involved in lipid, protein, and carbohydrate or starch biosynthesis). Other genes include those encoding pharmaceutically useful compounds, and genes encoding plant resistance products to combat fungal or other infections of the seed.

The puroindoline gene promoters can also be used to initiate transcription of mRNA molecules to inhibit expression of an endogenous puroindoline gene. Means for inhibiting gene expression in plants using recombinant DNA techniques are well known. For instance, antisense technology can be conveniently used see, e.g., Sheehy, et al., *Proc. Nat'l Acad. Sci. USA* 85:8805–8809 (1988), and U.S. Pat. No. 4,801,340. Catalytic RNA molecules or ribozymes can also be used to inhibit expression of endosperm-specific genes. The design and use of target RNA-specific ribozymes is described in Haseloff, et al., *Nature* 334:585–591 (1988). Introduction of nucleic acid configured in the sense orientation has also been shown to be an effective means by which to block the transcription of target genes. For an example of the use of sense suppression to modulate expression of endogenous genes see, Napoli, et al., *The Plant Cell* 2:279–289 (1990), and U.S. Pat. Nos. 5,034,323, 5,231,020, and 5,283,184.

The puroindoline promoters of the invention are typically at least about 400 base pairs in length, and often at least about 800 or about 1000 base pairs. The length of the promoters is typically less than about 3500 base pairs, usually less than about 2800 base pairs and often less than about 2000 base pairs in length. The length of the promoters is counted upstream from the translation start codon of the native gene. One of skill will recognize that use of the "about" to refer to lengths of nucleic acid fragments is meant to include fragments of various lengths that do not vary significantly from the lengths recited here and still maintain the functions of the claimed promoters (i.e., seed-specific gene expression).

To identify puroindoline promoters, the 5' portions of a genomic puroindoline gene clone is analyzed for sequences characteristic of promoter sequences. For instance, promoter sequence elements include the TATA box consensus sequence (TATAAT), which is usually 20 to 30 base pairs upstream of the transcription start site. In plants, further upstream from the TATA box, at positions −80 to −100, there is typically a promoter element with a series of adenines surrounding the trinucleotide G (or T) N G. Messing et al., *Genetic Engineering in Plants*, Kosage, et al. (eds.), pp. 221–227 (1983).

In preparing expression vectors of the invention, sequences other than the promoter and the puroindoline gene are also preferably used. If proper polypeptide expression is desired, a polyadenylation region at the 3'-end of the puroindoline coding region should be included. The polyadenylation region can be derived from the natural gene, from a variety of other plant genes, or from T-DNA.

The vector comprising the sequences from the puroindoline genes will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon, or phosphinothricin (the active ingredient in bialaphos and Basta).

III. PREPARATION OF TRANSGENIC PLANTS

In a preferred embodiment of this invention, the transgenic plants of this invention are cereal plants, including but not limited to, wheat, rye, triticale, barley, maize, sorghum and rice. In a more preferred embodiment, the transgenic plants are wheat, sorghum and maize. In a most preferred embodiment, the transgenic plant is maize.

The DNA constructs described above may be introduced into the genome of the desired plant host by a variety of conventional techniques. Techniques for transforming a wide variety of higher plant species are well known and described in the technical and scientific literature. See, for example, Weising, et al., *Ann. Rev. Genet.* 22:421–477 (1988).

The DNA construct may be introduced directly into the genomic DNA of the plant cell using techniques such as biolistic methods, electroporation, PEG poration, and microinjection of plant cell protoplasts or embryogenic callus. Alternatively, the DNA constructs may be combined with suitable T-DNA flanking regions and introduced using an *Agrobacterium tumefaciens* or *A. rhizogenes* vector.

Particle bombardment techniques are described in Klein, et al., *Nature* 327:70–73 (1987). A particularly preferred method of transforming wheat and other cereals is the bombardment of calli derived from immature embryos as described by Weeks, et al., *Plant Physiol.* 102:1077–1084 (1993).

Microinjection techniques are known in the art and well described in the scientific and patent literature. The introduction of DNA constructs using polyethylene glycol precipitation is described in Paszkowski, et al., *EMBO J.* 3:2717–2722 (1984). Electroporation techniques are described in Fromm, et al., *Proc. Nat'l Acad. Sci. USA* 82:5824 (1985).

*Agrobacterium tumefaciens*-meditated transformation techniques are also well described in the scientific literature. See, for example Horsch, et al., *Science* 233:496–498 (1984), and Fraley, et al. *Proc. Nat'l Acad. Sci. USA* 80:4803 (1983). Although Agrobacterium is useful primarily in dicots, certain monocots can be transformed by Agrobacterium. For instance, Agrobacterium transformation of rice is described by Hiei, et al, *Plant J.* 6:271–282 (1994); U.S. Pat. No. 5,187, 073; U.S. Pat. No. 5,591,616; Li, et al., *Science in China* 34:54 (1991); and Raineri, et al., *Bio/Technology* 8:33 (1990). Xu, et al., *Chinese J. Bot.* 2:81 (1990) transformed maize, barley, triticale and asparagus by Agrobacterium infection.

The present invention is particularly useful in wheat and other cereals. A number of methods of transforming cereals have been described in the literature. For instance, transformation of rice is described by Toriyama, et al., *Bio/Technology* 6:1072–1074 (1988), Zhang, et al., *Theor. Appl. Gen.* 76:835–840 (1988), and Shimamoto, et al., *Nature* 338:274–276 (1989). Transgenic maize regenerants have been described by Fromm, et al., *Bio/Technology* 8:833–839 (1990) and Gordon-Kamm, et al., *Plant Cell* 2:603–618 (1990)). Similarly, oats (Sommers, et al., *Bio/Technology* 10:1589–1594 (1992)), wheat (Vasil, et al., *Bio/Technology* 10:667–674 (1992)); Weeks, et al., *Plant Physiol.* 102:1077–1084 (1993)), sorghum (Casas, et al., *Proc. Nat'l Acad. Sci. USA* 90:11212–11216 (1993)), rice (Li, et al., *Plant Cell Rep.* 12:250–255 (1993)), barley (Yuechun & Lemaux, *Plant Physiol.* 104:37–48 (1994)), and rye (Castillo, et al., *Bio/Technology* 12:1366–1371 (1994)) have been transformed via bombardment.

Transformed plant cells that are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the puroindoline polynucleotide sequences. Plant regeneration from cultured protoplasts is described in Evans, et al., *Protoplasts Isolation and Culture, Handbook of Plant Cell Culture*, Macmillian Publishing Company, New York, pp. 124–176 1983; and Binding, *Regeneration of Plants, Plant Protoplasts*, CRC Press, Boca Raton, pp. 21–73 1985. Regeneration can also be obtained from plant callus, explants, organs, or parts thereof. Such regeneration techniques are described generally in Klee, et al. *Ann. Rev. of Plant Phys.* 38:467–486 (1987).

The methods of the present invention are particularly useful for incorporating the puroindoline polynucleotides into transformed plants in ways and under circumstances which are not found naturally. In particular, the puroindoline proteins may be expressed at times or in quantities which are not characteristic of natural plants.

One of skill will recognize that after the expression cassette is stably incorporated in transgenic plants and confirmed to be operable, it can be introduced into other plants by sexual crossing. A technique used to transfer a desired phenotype to a breeding population of plants is through backcrossing. However, any of a number of standard.breeding techniques can be used, depending upon the species to be crossed.

IV. DISRUPTION OF THE PUROINDOLINE GENES

In one embodiment of this invention, plants which express puroindoline genes and possess soft textured grain are transformed so that there is a disruption between the DNA-RNA-protein synthesis cellular pathway. Inhibition of puroindoline protein synthesis can be done by a variety of different mechanisms, including but not limited to, antisense nucleic acids, transposon, ribozymes, site specific mutagenesis, chemical mutagenesis and irradiation. In a preferred embodiment, inhibition of protein synthesis is with antisense nucleic acids.

Antisense technology is based on inverting the sense nucleic acid relative to its normal presentation for transcription and operably linking it to a promoter. The antisense nucleic acid may be constructed using the methods described above, provided that it is capable of being transcribed into RNA which is complimentary to and capable of blocking translation of the RNA produced by the sense gene. For a complete discussion of antisense nucleic acids and methodologies of making antisense and using it to block inhibit translation of RNA, see U.S. Pat. No. 5,728,926, issued Mar. 17, 1998 and U.S. Pat. No. 5,695,992, issued Dec. 9, 1997.

In brief, the antisense genes are produced by excising the double stranded coding region of the sense gene or a functional fragment thereof and inserting it downstream from a promoter in an inverted orientation relative to its normal presentation for transcription. Preferably, a terminator structure is added to what will be the 3' end of the antisense gene. In addition, the antisense gene can be made synthetically, particularly if a small fragment of the sense gene is to be used. The antisense nucleic acid with its promoter and terminator sequences are ligated into a vector and the vector is introduced into a plant according to techniques well known to those of skill and described above.

Ribozymes are another nucleic acid based inhibitor of translation. There are two different types of ribozymes. The first occurs naturally in *Tetrahymena thermophila* (known as the IVS, or L-19 IVS RNA) and has been extensively described in Zaug, et al., *Science* 224:574–578 (1984); Zaug, & Cech, *Science* 231:470–475 (1986); Zaug, et al., *Nature* 324:429–433 (1986); and P.C.T Application No. WO 88/04300. The active sites of these ribozymes consist of eight base pairs which hybridize to a target RNA sequence. The ribozyme, in the presence of free guanosine or guanosine derivatives, then cleaves the target RNA. The RNA fragments which arise from cleavage contain terminal 5' phosphate and 3' hydroxyl groups.

The second class of ribozymes is described in U.S. Pat. No. 5,747,335, issued May 5, 1998. This class of ribozymes comprises a hybridizing region comprising one or more arms formed of single stranded RNA with a sequence complementary to at least part of a target RNA. At least one of the arms is associated with a catalytic region capable of cleaving the target RNA and contains at least nine nucleotides. If the hybridizing region comprises two or more arms of RNA, the sum of nucleotides in the arms should be greater than nine nucleotides.

Yet another technique to inhibit protein synthesis is to introduce a transposon into the plant's genome. This methodology is described in U.S. Pat. No. 5,225,341, issued Jul. 6, 1993. Briefly, insertion of a transposon disrupts the gene of interest, for example, puroindoline A. Currently, the most preferred transposon system is the Ac/Ds system from maize, although elements from other species may also be used. Many plants, however, are known to contain transposons. They are typically detected by variegation arising from somatic mutation. A review of transposons can be found in Nevers, et al., *Adv. in Bot. Res.* 12:103–203 (1987).

The desired vector will preferably comprise a transposon containing an expression cassette designed for initiating transcription of the gene of interest in plants. Ancillary sequences, of bacterial or viral origin, are also typically included to allow the vector to be cloned in a bacterial or phage host.

The vector will also typically contain an ancillary selectable marker gene by which transformed plant cells can be identified in culture. Usually, the marker gene will encode antibiotic resistance. Other ancillary DNA sequences encoding additional functions may also be present in the vector. For instance, in the case of Agrobacterium transformations, T-DNA sequences will also be included for subsequent transfer to plant chromosomes.

In addition to the nucleic acid-based strategies outlined above, other methods of inhibiting synthesis of proteins by plants are known to those of skill. These methods include, but are not limited to, chemical mutagenesis and irradiation. Chemical mutagenesis is the contacting of a chemical to the cells of a plant so that the strands of DNA are damaged. The cell then uses its own repair mechanism to anneal the strands of DNA during the next doubling of chromosomes in preparation for cell division. However, the repair mechanism often is not perfect and mismatches in the double stranded DNA occur. When the cells divide, one of the daughter cells contains the mismatched DNA and therefore the mutation.

Irradiation also results in mutations. Plant cells are preferably irradiated with X-rays, however, ultra violet radiation also causes breaks in the DNA strands. Similarly to chemical mutagenesis, the imperfect repair machinery of the cell creates mutations in the daughter cells. When these cells are used to generate plants, the mutation is present in the genome and can be passed on to future generations.

V. SELECTIVE BREEDING OF PLANTS

After transgenic plants are produced, it is beneficial in selecting subsequent generations to select progeny which contain genetic material which confers a specific beneficial trait, e.g., grain texture. Before selection can begin, however, a genetic map of the desirable genome should be made. Genetic mapping is done by finding polymorphic markers that are genetically linked to each other (in linkage groups) or linked to genes or QTL affecting phenotypic traits of interest. The alignment of markers into linkage groups is useful as a reference for future use of the markers and for accurately positioning genes or QTL relative to the markers. Many of these QTL's have multiple sub-loci and haplotypes across the sub-loci. Each haplotype provides a different allele composition within a locus, thereby expanding the utility of these marker loci to more mapping studies than possible with only two alleles per locus.

A. Characterization of Plants

The progeny and transgenic plants of this invention can be characterized either genotypically or phenotypically. Genotypic analysis is the determination of the presence or absence of particular genetic material. To determine whether puroindoline genes have been successfully introduced into progeny plants, the parent(s) of the plants of this invention are also analyzed genotypically.

Phenotypic analysis is the determination of the presence or absence of a phenotypic trait. A phenotypic trait is a physical characteristic of a plant determined by the genetic material of the plant in concert with environmental factors. Phenotypic traits can either be simple, e.g.,Mendelian, or complex, e.g., quantitative. Mendelian traits are those conferred upon the hybrid plant by dominant genes. For example, requirement for vernalization. The requirement (winter habit) is recessive to no requirement (spring habit).

A quantitative phenotypic trait is one wherein the physical characteristic of the progeny plant is intermediate between the physical trait of the two parents. For purposes of this discussion only, the parents of a transgenic plant are the genome donor and the puroindoline gene donor. An example of a quantitative trait is grain texture in wheat.

1. DNA Analysis a. DNA Fingerprinting

In general, "DNA fingerprinting" is a broad term used to designate methods for assessing sequence differences in DNA isolated from various sources. Typically, DNA fingerprinting is used to analyze and compare DNA from different species of organisms. In a preferred embodiment of this invention, DNA fingerprinting is used to assess the relationship of individuals, particularly parents, progeny and transgenic plants.

DNA sequence differences detected by fingerprinting are referred to as DNA polymorphisms. The presence of a DNA polymorphism in an organism's DNA can serve to indicate the genetic origin of such an organism and serve as a characteristic genetic marker of that organism. Such polymorphisms can result from insertion, deletion, and/or mutation events in the genome.

Many methods are known in the art for DNA fingerprinting. The restriction fragment length polymorphism (RFLP) technique employs restriction enzyme digestion of DNA, followed by size separation of the digested DNA by gel electrophoresis, and hybridization of the size-separated DNA with a specific polynucleotide fragment (or "polynucleotide probe"). As used herein, a "probe" is a biochemical labeled with a radioactive isotope or tagged in other ways for ease in identification. A probe is used to identify a specific region of DNA, a gene, a gene product or a protein. Thus a "polynucleotide probe" is a nucleic acid molecule that can be used to identify complementary nucleic acid sequences. The sequence of the polynucleotide probe may or may not be known. Differences in the size of the restriction fragments to which the polynucleotide probe binds reflect sequence differences in DNA samples, or DNA polymorphisms. See Tanksley, *Biotechnology* 7:257–264 (1988). Thus, a "polymorphic DNA fragment," is a DNA fragment which has a unique size and sequence, and is either present in other DNA samples with another unique size or is not present in other DNA samples.

Other fingerprinting methods generate DNA fragments for fingerprint analysis using polymerase chain reaction (PCR) amplification of specific DNA sequences. See, e.g. Williams, *Nucl. Acids Res.* 18:6531–6353 (1990) (random amplified polymorphic DNA (RAPD) technique), Heath, *Nucl. Acids Res.* 21:5782–5785 (simple sequence repeat (SSR) technique), and PCT application WO 93/06239 (amplified fragment length polymorphism (AFLP) technique). See also U.S. Pat. No. 4,683,195 and U.S. Pat. No. 4,683,202 (discussing PCR amplification techniques).

A useful technique for analyzing the presence of transferred genetic markers, RAPD analysis is used to analyze the genotypic information of the progeny plants of this invention. RAPD analysis detects recombination events at the genome level and is based on the detection of specific but randomly generated fragments of DNA. Because it does not require labeled nucleic acid probes or hybridization as described above, it can be quickly performed.

Briefly, the genomic DNA is isolated from the parents and the progeny. Each genomic DNA sample is amplified with sets of primers. The amplification products are then electrophoresed in an agarose gel to generate DNA profiles. Agarose electrophoresis of DNA is well known in the field. If desired, the PCR primers can be labeled with radioisotopes or fluorophores for better detection of low concentrations of DNA. However, usually enough DNA fragments are generated in the amplification step so that labeling is not necessary and the DNA profile can be visualized by staining the gel with Ethidium Bromide, again, a standard procedure.

If the profile in the lane with the maternal DNA is identical to the profile in the lane with the progeny's DNA, then no exchange of DNA has occurred and the progeny is a result of a self fertilization or cloning. If the DNA profile of the progeny is different in any way from the DNA profile of the maternal parent, then rearrangement of the genome has occurred.

All of these PCR-based fingerprinting methods result in the generation of a large number of reproducible DNA fragments of specific size and sequence that can be separated according to size, typically by gel electrophoresis. Visualization of the size-separated fragments is effected either by direct visualization with a fluorescent dye, by hybridization with a labeled polynucleotide probe, or by labeling the amplification products during PCR (radioactively or fluorescently) followed by detection of the labeled products in the gel.

b. Making and Using Markers for Detection of Polymorphic Nucleic Acids

Although DNA sequences which code for necessary proteins are well conserved across a species, there are regions of DNA which are non-coding or code for portions of proteins which do not have critical functions and therefore, absolute conservation of nucleic acid sequence is not strongly selected. The major causes of genetic variability are addition, deletion or point mutations, recombination and transposable elements within the genome of individuals in a plant population.

Point mutations are typically the result of inaccuracy in DNA replication. During meiosis in the creation of germ cells or in mitosis to create clones, DNA polymerase "switches" bases, either transitionally (i.e., a purine for a purine and a pyrimidine for a pyrimidine) or transversionally (i.e., purine to pyrimidine and vice versa). The base switch is maintained if the exonuclease function of DNA polymerase does not correct the mismatch. At germination, or the next cell division (in clonal cells), the DNA strand with the point mutation becomes the template for a complementary strand and the base switch is incorporated into the genome.

Transposable elements are sequences of DNA which have the ability to move or to jump to new locations within a genome. Several examples of transposons are known in the art (see, e.g., Freeling M., *Ann. Rev. Plant. Physiol.* 35:277–298 (1984); Haring, et al., *Plant Mol. Biol.* 16:449–469 (1991); and Walbot, *Ann. Rev. Plant Mol. Biol.* 43:49–82 (1992)).

One of skill can generate probe nucleic acids for detecting markers, including probes which are PCR primers, allele-specific probes, RAPD probes and the like for the detection of polymorphic nucleotides at the loci disclosed herein, as well as the genetically linked sequences discussed below. Examples of appropriate cloning and sequencing techniques, and instructions sufficient to direct persons of skill through many cloning exercises are found in Berger and Kimmel, *Guide to Molecular Cloning Techniques, Methods in Enzymology* Vol. 152 Academic Press, Inc., San Diego, Calif. (Berger); Sambrook et al., *Molecular Cloning—A Laboratory Manual* (2nd ed.) Vol. 1–3, Cold Spring Harbor Laboratory, Cold Spring Harbor Press, NY (1989), (Sambrook); and *Current Protocols in Molecular biology*, F. M. Ausubel et al., eds., Current Protocols, a joint venture between Greene Publishing Associates, Inc. and John Wiley & Sons, Inc., (through and including the 1997 Supplement) (Ausubel). A catalogue of Bacteria and Bacteriophages useful for cloning is provided, e.g., by the ATCC, e.g., *The ATCC Catalogue of Bacteria and Bacteriophage*, Gherna et al. (eds) (1992) published by the ATCC. Additional basic procedures for sequencing, cloning and other aspects of molecular biology and underlying theoretical considerations are also found in Lewin, *Genes V*, Oxford University Press Inc., NY (1995) (Lewin); and Watson et al., *Recombinant DNA, 2nd ed.*, Scientific American Books, NY (1992).

Product information from manufacturers of biological reagents and experimental equipment also provide information useful in known biological methods. Such manufacturers include the Sigma Chemical Company (Saint Louis, Mo.); New England Biolabs (Beverly, Mass.); R&D systems (Minneapolis, Minn.); Pharmacia LKB Biotechnology (Piscataway, N.J.); CLONTECH Laboratories, Inc. (Palo Alto, Calif.); ChemGenes Corp., (Waltham Mass.) Aldrich Chemical Company (Milwaukee, Wis.); Glen Research, Inc.

(Sterling, Va.); GIBCO BRL Life Technologies, Inc. (Gaithersberg, Md.); Fluka Chemica-Biochemika Analytika (Fluka Chemie AG, Buchs, Switzerland); Invitrogen (San Diego, Calif.); Perkin Elmer (Foster City, Calif.); and Stratagene; as well as many other commercial sources known to one of skill.

The nucleic acid compositions of this invention, whether DNA, RNA, cDNA, genomic DNA, or analogs thereof, or a hybrid of these molecules, are isolated from biological sources or synthesized in vitro. The nucleic acids of the invention are present in plants, whole cells, cell lysates or in partially purified or substantially pure form.

In vitro amplification techniques suitable for amplifying sequences for use as molecular probes or generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as U.S. Pat. No. 4,683,202; *PCR Protocols a Guide to Methods and Applications* (Innis et al. eds) Academic Press Inc. San Diego, Calif. (1990) (Innis); Arnheim & Levinson (Oct. 1, 1990) *C&EN* 36–47; Kwoh et al., *Proc. Nat'l Acad. Sci. USA* 86:1173 (1989); Guatelli et al., *Proc. Nat'l Acad. Sci. USA* 87:1874 (1990); Lomell et al., *J. Clin. Chem.* 35:1826 (1989); Landegren et al., *Science* 241:1077–1080 (1988); Van Brunt, *Biotechnology* 8:291–294 (1990); Wu & Wallace, *Gene* 4:560 (1989); Barringer et al., *Gene* 89:117 (1990), and Sooknanan & Malek, *Biotechnology* 13: 563–564 (1995). Improved methods of cloning in vitro amplified nucleic acids are described in Wallace et al., U.S. Pat. No. 5,426,039. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

Oligonucleotides for use as probes, e.g., in in vitro amplification methods, for use as gene probes, or as inhibitor components (e.g., ribozymes) are typically synthesized chemically according to the solid phase phosphoramidite triester method described by Beaucage & Caruthers, *Tetrahedron Letts.*, 22(20):1859–1862 (1981), e.g., using an automated synthesizer, as described in Needham-VanDevanter et al., *Nucl. Acids Res.*, 12:6159–6168 (1984). Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson & Regnier, *J. Chrom.* 255:137–149 (1983). The sequence of the synthetic oligonucleotides can be verified using the chemical degradation method of Maxam & Gilbert, *Methods in Enzymology* 65:499–560 (1980).

c. Labeling and Detecting Probes

A probe for use in an in situ detection procedure, an in vitro amplification procedure (PCR, LCR, etc.), hybridization techniques (allele-specific hybridization, in situ analysis, Southern analysis, northern analysis, etc.) or any other detection procedure herein can be labeled with any composition detectable by spectroscopic, photochemical, biochemical, immunochemical, electrical, optical or chemical means. Useful labels in the present invention include spectral labels such as fluorescent dyes (e.g., fluorescein isothiocyanate, Texas red, rhodamine, dixogenin, biotin, and the like), radiolabels (e.g., $^{3}$H, $^{125}$I, $^{35}$S, $^{14}$C, $^{32}$P, $^{33}$P, etc.), enzymes (e.g., horse-radish peroxidase, alkaline phosphatase etc.) and other labels known to those skilled in the art.

In general, a detector which monitors a probe-target nucleic acid hybridization is adapted to the particular label which is used. Typical detectors include spectrophotometers, phototubes and photodiodes, microscopes, scintillation counters, cameras, film and the like, as well as combinations thereof. Examples of suitable detectors are widely available from a variety of commercial sources known to persons of skill.

Because incorporation of radiolabeled nucleotides into nucleic acids is straightforward, this detection represents a preferred labeling strategy. Exemplary technologies for incorporating radiolabels include end-labeling with a kinase or phosphatase enzyme, nick translation, incorporation of radio-active nucleotides with a polymerase and many other well known strategies.

Fluorescent labels are also preferred labels, having the advantage of requiring fewer precautions in handling. Preferred labels are typically characterized by one or more of the following: high sensitivity, high stability, low background, low environmental sensitivity and high specificity in labeling. Fluorescent moieties, which are incorporated into the labels of the invention, are generally are known, including but not limited to, Texas red, rhodamine and fluorescein. Individual fluorescent compounds which have functionalities for linking to an element desirably detected in an apparatus or assay of the invention, or which can be modified to incorporate such functionalities include, e.g., dansyl chloride; fluoresceins such as 3,6-dihydroxy-9-phenylxanthydrol. Many fluorescent tags are commercially available from SIGMA chemical company (St. Louis, Mo.), Molecular Probes, R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.) as well as other commercial sources known to one of skill.

2. Morphological and Quantitative Trait Study

The general appearance of progeny and transgenic plants is also used to characterize the plants of this invention. The morphological traits of grain texture and expression of puroindolines are monitored throughout the generations of progeny. In addition, he quantitative traits of plant height, ear length (in maize), and leaf shape are also monitored to ensure the plant line remains healthy.

This quantitative trait data are significant for the identification of the heterotic expression or depression in the progeny. For confidence, at least two but preferably twenty observations of each quantitative trait of each parent and the progeny are subjected to an analysis of variance. The results of each plant for various traits with a least significant difference (LSD) at 5% and the coefficient of variation are then determined and tabulated.

In addition to heterosis expression and depression in the progeny, differences in quantitative traits can indicate recombination at the genetic level. Cytology of the parents and progeny can also be compared to characterize the hybrid progeny. Cytological analysis includes but is not limited to, chromosome painting to determine the presence of parentally derived chromosomes in the hybrid progeny and in situ hybridization for, e.g., isozyme analysis.

Fluorescence in situ hybridization (FISH) is an important technique for visualizing DNA sequences. The method is now in routine use in research laboratories for gene localization studies. For example, FISH is used to map genes to specific chromosome regions or to order clones along chromosomes to create. In addition, FISH can also be used to compare parental and progeny chromosomes.

A class of FISH probes termed "chromosome paints" are available. This type of probe is very useful for determining chromosome structure, as they more or less uniformly hybridize to the entire length of a given chromosome. Paints are used to determine chromosome complements of a cell, structural abnormalities such as translocations, and to identify the parental origin of marker chromosomes.

Numerous methods are available to label DNA probes for use in FISH, including indirect methods whereby a hapten such as biotin or digoxigenin is incorporated into DNA using enzymatic reactions. Following hybridization to a metaphase chromosome spread or interphase nuclei, a fluorescent label is attached to the hybrid through the use of immunological methods. More recently, fluorescent dyes have been directly incorporated into probes and detected without the use of an intermediate step. Standard FISH dyes include fluorescein, rhodamine, Texas Red and Cascade Blue. Multiprobe FISH analysis can be accomplished by labeling different probes with different haptens or fluorescent dyes.

B. Allele-Specific Hybridization (ASH)

One especially preferred technique for screening progeny for particular sequences conferred upon it by its parents is allele-specific hybridization, or "ASH." This technology is based on the stable annealing of a short, single-stranded oligonucleotide probe to a single-stranded target nucleic acid only when base pairing is completely complementary. The hybridization can then be detected from a radioactive or non-radioactive label on the probe (methods of labeling probes and other nucleic acids are set forth in detail below).

ASH markers are polymorphic when their base composition at one or a few nucleotide positions in a segment of DNA is different among different genotypes. For each polymorphism, two or more different ASH probes are designed to have identical DNA sequences except at the polymorphic nucleotide(s). Each probe will have exact homology with one allele sequence so that the complement of probes can distinguish all the alternative allele sequences. Each probe is hybridized against the target DNA. With appropriate probe design and stringency conditions, a single-base mismatch between the probe and target DNA will prevent hybridization and the unbound probe will wash away. In this manner, only one of the alternative probes will hybridize to a target sample that is homozygous or homogeneous for an allele (an allele is defined by the DNA homology between the probe and target). Samples that are heterozygous or heterogeneous for two alleles will hybridize to both of two alternative probes. Having a probe for each allele allows the polymorphism to be genetically co-dominant which is useful in determining zygosity. In addition, a co-dominant ASH system is useful when hybridization does not occur for either one of two alternative probes, so that control experiments can be directed towards verifying insufficient target DNA or the occurrence of a new allele.

ASH markers are used as dominant markers where the presence or absence of only one allele is determined from hybridization or lack of hybridization by only one probe. The alternative allele may be inferred from the lack of hybridization. Heterogeneous target nucleic acids (i.e., chromosomal DNA from a multiallelic plant) are detected by monitoring simultaneous hybridization of two or more probes comprising different polymorphic nucleotides to a genomic nucleic acid.

An ASH probe is designed to form a stable duplex with a nucleic acid target only when base pairing is completely complementary. One or more base-pair mismatches between the probe and target prevents stable hybridization. This holds true for numerous variations of the process. The probe and target molecules are optionally either RNA or denatured DNA; the target molecule(s) is/are any length of nucleotides beyond the sequence that is complementary to the probe; the probe is designed to hybridize with either strand of a DNA target; the probe ranges in size to conform to variously stringent hybridization conditions, etc.

The polymerase chain reaction (PCR) (see, e.g., Mullis & Faloona, *Methods Enzymol* 155:335–350 (1987) and references supra) allows the target sequence for ASH to be amplified from low concentrations of nucleic acid in relatively small volumes (Koenraadt & Jones, *Phytopatholog* 82:1354–1358 (1992); Iitiä et al., *BioTechniques* 17:566–571 (1994)). Otherwise, the target sequence from genomic DNA is digested with a restriction endonuclease and size separated by gel electrophoresis. Hybridizations typically occur with the target sequence bound to the surface of a membrane or, as described in U.S. Pat. 5,468,613, the ASH probe sequence may be bound to a membrane.

Utilizing nucleotide alleles and polymorphisms, ASH data can be obtained by amplifying nucleic acid fragments from genomic DNA using PCR, transferring the target DNA to a membrane in a dot-blot format, hybridizing a labeled oligonucleotide probe to the target, and observing the hybridization dots by autoradiography.

In one variant, ASH technologies are adapted to solid phase arrays for the rapid and specific detection of multiple polymorphic nucleotides. Typically, an ASH probe is linked to a solid support and a target nucleic acid (e.g., a genomic nucleic acid) is hybridized to the probe. Either the probe, or the target, or both, can be labeled, typically with a fluorophore. Where the target is labeled, hybridization is detected by detecting bound fluorescence. Where the probe is labeled, hybridization is typically detected by quenching of the label. Where both the probe and the target are labeled, detection of hybridization is typically performed by monitoring a color shift resulting from proximity of the two bound labels. A variety of labeling strategies, labels, and the like, particularly for fluorescent based applications are described, supra.

In one embodiment, an array of ASH probes are synthesized on a solid support. Using chip masking technologies and photoprotective chemistry it is possible to generate ordered arrays of nucleic acid probes. These arrays, which are known, e.g., as "DNA chips," or as very large scale immobilized polymer arrays ("VLSIPS™" arrays) can include millions of defined probe regions on a substrate having an area of about 1 $cm^2$ to several $cm^2$.

The construction and use of solid phase nucleic acid arrays to detect target nucleic acids is well described in the literature. See, Fodor et al., *Science* 251:767–777 (1991); Sheldon et al., *Clin. Chem.* 39(4):718–719 (1993); Kozal et al., *Nature Medicine* 2(7): 753–759 (1996) and U.S. Pat. No. 5,571,639. See also, PCT/US95/16155 (WO 96/17958). In brief, a combinatorial strategy allows for the synthesis of arrays containing a large number of probes using a minimal number of synthetic steps. For instance, it is possible to synthesize and attach all possible DNA 8mer oligonucleotides ($4^8$, or 65,536 possible combinations) using only 32 chemical synthetic steps. In general, VLSIPS™ procedures provide a method of producing $4^n$ different oligonucleotide probes on an array using only 4n synthetic steps.

Light-directed combinatorial synthesis of oligonucleotide arrays on a glass surface is performed with automated phosphoramidite chemistry and chip masking techniques similar to photoresist technologies in the computer chip industry. Typically, a glass surface is derivatized with a silane reagent containing a functional group, e.g., a hydroxyl or amine group blocked by a photolabile protecting group. Photolysis through a photolithogaphic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents. Monitoring of hybridization of target nucleic acids to the array is typically performed with fluorescence microscopes or laser scanning microscopes.

In addition to being able to design, build and use probe arrays using available techniques, one of skill is also able to order custom-made arrays and array-reading devices from manufacturers specializing in array manufacture.

It will be appreciated that probe design is influenced by the intended application. For example, where several allele-specific probe-target interactions are to be detected in a single assay, e.g., on a single DNA chip, it is desirable to have similar melting temperatures for all of the probes. Accordingly, the length of the probes are adjusted so that the melting temperatures for all of the probes on the array are closely similar (it will be appreciated that different lengths for different probes may be needed to achieve a particular $T_m$ where different probes have different GC contents). Although melting temperature is a primary consideration in probe design, other factors are optionally used to further adjust probe construction.

C. Marker Assisted Selection

After genes or a QTL and a marker or markers are mapped together and found to be in linkage disequilibrium, it is possible to use those markers to select for the desired alleles of those genes or QTL—a process called marker-assisted selection (MAS). In brief, a nucleic acid corresponding to the marker nucleic acid is detected in a biological sample from a plant to be selected. This detection can take the form of hybridization of a probe nucleic acid to a marker, e.g., using allele-specific hybridization, Southern analysis, northern analysis, in situ hybridization, hybridization of primers followed by PCR amplification of a region of the marker or the like. A variety of procedures for detecting markers are described herein. After the presence (or absence) of a particular marker in the biological sample is verified, the plant is selected, i.e., used to make progeny plants by selective breeding.

Another use of MAS in plant and animal breeding is to assist the recovery of the recurrent parent genotype by backcross breeding. MAS for the recurrent-parent genotype can be combined with MAS for the desired genetic material using these markers. Accordingly, it is possible to use the markers to introduce QTLs into cereal plants having an otherwise desirable genetic background using the markers of the invention for selection of the QTL and for selection of the otherwise desirable background.

Any of the cloning or amplification strategies described above are useful for creating contiguous sequences (contigs) of overlapping clones, thereby providing overlapping nucleic acids which show the physical relationship at the molecular level for genetically linked nucleic acids. A common example of this strategy is found in whole organism sequencing projects, in which overlapping clones are sequenced to provide the entire sequence of a chromosome. In this procedure, a library of the organism's cDNA or genomic DNA is made according to standard procedures described, e.g., in the references above. Individual clones are isolated and sequenced, and overlapping sequence information is ordered to provide the sequence of the organism. See also, Fleischmann et al., *Science* 269:496–512 (1995) describing whole genome random sequencing and assembly of the complete *Haemophilus influenzae* genome; Fraser et al., *Science* 270:397–403 (1995) describing whole genome random sequencing and assembly of the complete *Mycoplasma genitalium* genome and Bult et al., *Science* 273:1058–1073 (1996) describing whole genome random sequencing and assembly of the complete *Methanococcus jannaschii* genome. Hagiwara & Curtis, *Nucl. Acids Research* 24(12):2460–2461 (1996) developed a "long distance sequencer" PCR protocol for generating overlapping nucleic acids from very large clones to facilitate sequencing, and methods of amplifying and tagging the overlapping nucleic acids into suitable sequencing templates. The methods can be used in conjunction with shotgun sequencing techniques to improve the efficiency of shotgun methods typically used in whole organism sequencing projects.

As applied to the present invention, the techniques are useful for identifying and sequencing genomic nucleic acids genetically linked to the loci described.

VI. EXAMPLES

A. Plant Culture and Measurement of Grain Hardness

Soft and hard near isogenic lines (NILs) of *T. aestivum*, "Falcon" and "Heron" varieties (Symes, et al., *Aust J. Agric. Res.* 20, 971–979 (1969)) were grown near Lind, Wash. in the summer of 1995. Grain hardness was measured using a near-infrared reflective (NIR) spectrometer (model 450, Technicon, Tarrytown, N.Y.), on UDY ground grain (Method 39-70A; AACC 1995). Single kernel hardness readings (SKCS) were obtained by analyzing 300 kernel samples of grain for hardness using the Perten Model SKCS 4100 following the manufacturer's suggested operating procedure (Perten Instruments, Reno, Nev.).

Eighty-three homozygous chromosome 5D substitution lines were developed from the soft red wheat "Chinese Spring" and the hard red winter wheat cultivar "Cheyenne" following the procedure of Law, *Genetics* 53:487 (1966). The puro B from "Cheyenne" has a serine at position 46. Each line contained 20 pairs of normal euploid "Chinese Spring" (CS) chromosomes and 1 pair of recombined "Chinese Spring"/"Cheyenne" 5D chromosomes (CS(CNN5D)). "Langdon" durum, the "Langdon" substitution line LDN 5D(5B) where the 5D chromosome of "Chinese Spring" has replaced chromosome 5B, and CS Nulli 5D/Tetra 5A where the 5D chromosome of "Chinese Spring" has been replaced with another copy of the 5A chromosome, were grown in a greenhouse under common culture practices.

TABLE 1

Grain Texture Determination

| Grain | SKCS | NIR |
|---|---|---|
| "Chinese Spring" (Soft) | 60 | |
| CS(CNN5D) (Hard) | 79 | |
| "Langdon" (Very Hard) | 88 | |
| LDN 5D(5B) (Soft) | 24 | |
| "Wanser" (Hard) | 64 | |
| N 5D/T 5A (Hard) | 77 | |
| "Heron" (Soft) | 21 | |
| "Falcon" (Hard) | 61 | |
| Oat (Soft) | −26 | 41 |
| Oat (Soft) | −54 | |
| Barley (Hard) | 72 | 20 |
| Maize (Popcorn) (Hard) | | 132 |
| Brown Rice (Hard) | | 141 |

From Table 1, it can be seen that the transfer of a mutant puro B protein from the hard grain variety "Cheyenne" caused the grain in a progeny plant (CS(CNN5D)) to be significantly harder than the grain from the parent line "Chinese Spring." The SKCS value for the progeny plant was found to be 79 and that of the parent was 60. Conversely, the appearance of puro A and puro B from "Chinese Spring" in the "Langdon" durum wheat caused the SKCS value of the grain to drop from 88 to 24; essentially creating a soft durum wheat.

As described above, some of the hard wheat varieties lack the puro B serine mutation. "Falcon", one such variety, was chosen for further study. Complementary soft and hard NILs were derived using "Falcon" as the hard allele donor and "Heron" as the soft allele donor (Symes, *Aust. J. Agric. Res.* 16:113–123 (1965)). In this set of NILs, soft and hard lines existed where either "Falcon" or "Heron" served as the recurrent parent. NILs of each set were created by seven generations of backcrossing and selecting for either soft or hard textured grain. The NILs shown in FIG. 1 represent one hard and one soft NIL each created using either "Falcon" or "Heron" as the recurrent parent.

The linkage between the presence or absence of puro A protein and grain softness/hardness was tested. Each of the 44 "Falcon"/"Heron" hard/soft NILs was characterized by separating friabilin component proteins on SDS PAGE (as described below) and scoring presence of puro A protein. The NILs were also characterized as to puro A gene content based on the capability of amplifying puro A from genomic DNA (as described below). Individual lines were classified as being "Falcon" type with puro A absent (null), or "Heron" type with puro A present. A graph of phenotypic grain hardness of these NILs by two different methods is shown in FIG. 1 with the puro A type indicated. Two NILs were found to be mixtures of seeds containing puro A and those lacking the protein. Ten individual kernels each of these two NILs (AUS 90077 and AUS 90254) were assayed for the presence of puro A. NIL AUS 90077, NIR hardness of 39, had six of ten kernels containing puro A. Assay of NIL AUS 90254, NIR hardness of 29, showed seven of ten kernels contained puro A. Based on the intermediate hardness values of these two NILs, the percent mixture closely fits the expected frequency. (Soft NIL average NIR equals 15. Hard NIL average NIR equals 71. NIL 90077 expected equals {(6× 15)+(4×71)}/10=37.4. NIL 90254 expected equals {(7×15)+ (4×71)}/10=31.8.) The observed percent mixture for each of these NILs then likely explains their somewhat intermediate hardness values. Consequently, there was no recombination between the presence of puro A and grain softness in this set of genetic stocks.

B. DNA Isolation and PCR Amplification of Puro A, Puro B and GSP-1

DNA from wheat endosperm was isolated by the procedure of Dellaporta, et al., *Plant Mol. Biol. Rep.* 1:19–21 (1983). A primer designed to recognize the serine sequence change present in puro B of the hard wheat cultivars "Wanser" and "Cheyenne" was used on 13 soft and 11 hard-textured wheats. The serine mutation in puro B is a change of amino acid 46 glycine (Gautier, et al., *Plant Molec. Biol.* 25:43–57 (1994)) (GGC) to serine (AGC). This sequence change was exploited to make glycine or serine specific PCR primers (Giroux & Morris, *Theor. Appl. Genet.* 95:857–864 (1997)) (SEQ ID NO:9 and 10). "Hard" or serine-specific 3' puro B primers end with T while the "soft" or glycine-specific primer 3' ends with C.

Amplification of puro B sequences with SEQ ID NO:9, SEQ ID NO:10 and SEQ ID NO:11 which are specific for the Gly-46 or Ser-46 in wheat varieties is described elsewhere (Giroux & Morris, *Theor. Appl. Genet.* 95:857–864 (1997)). Amplification of puro A sequences using SEQ ID NO:7 and SEQ ID NO:8 as primers were performed with the varieties of wheat as described previously (Gautier, et al., *Plant Molec. Biol.* 25:43–57 (1994)). Annealing temperature for both sets of primers was maintained at 58° C. Individual PCR reactions were replicated two or more times.

A size specific product (250 bp) detected with the hard serine specific primer (puro B) was taken as indicating the presence of serine in position 46. While the glycine to serine change in puro B is quite common among hard wheats, some exceptions were found. The majority (7 of 11) of the hard wheats exhibited a serine-specific 250 bp band, whereas four hard wheat varieties, "Express", "Butte 86", "Westbred 926" and "Falcon" did not. Each of these four exceptions exhibited a glycine-specific "soft" wheat puro B band. All 13 soft wheats produced the glycine-specific band and no serine-specific band. Amplification of the entire puro B coding sequence was possible for each of the genomic DNAs used.

A GSP-1 related clone, SR3.1, detects an RFLP that is apparently linked with grain hardness (Jolly, et al., *Proc. Nat'l Acad. Sci. USA* 93:2408–2413 (1996)), however no transcript or gene expression analysis has been reported. We performed northern analysis on "Heron", "Falcon", and the four hard/soft NILs used in our experiments, and found no consistent transcript level differences for GSP-1 related to grain hardness. Additionally, four individual hard and soft lines derived from "Chinese Spring" and CS(CNN5D) were examined.

Additional genes, termed GSP-1, have been suggested to be involved in grain softness (Rahman, et al., *Eur. J. Biochem.* 223:917–925 (1994); and Jolly, et al., *Proc. Nat'l Acad. Sci. USA* 93:2408–2413 (1996)). A GSP-1 probe was amplified by RT-PCR from RNA extracted from 14 days after flowering (DAF) kernels of "Chinese Spring." The probe was made with the following primers: The 5' primer consisted of the DNA sequence 5' GTAGTGAGCACTAC-TATTGC 3' (SEQ ID NO:11) and the 3' primer was the reverse complement of 5'-GAGCCTTCCCTCCAAGTGC-3' (SEQ ID NO:12). The PCR annealing temperature was 58° C.

SEQ ID NO:11 and SEQ ID NO:12 amplified an internal 400 bp fragment described as GSP1b (Rahman, et al., *Eur. J. Biochem.* 223:917–925 (1994)). This 400 bp fragment was used to probe at high stringency total RNA from "Falcon"/ "Heron" NILS and total RNA from "Chinese Spring" chromosome 5D substitution lines (Giroux & Morris, *Theor. Appl. Genet.* 95:857–864 (1997)).

As with the "Falcon"/"Heron" NILs, GSP-1 transcripts were present irrespective of grain hardness. "Langdon"

durum and the soft disomic substitution lines LND-CS DS5D(5B) also both had GSP-1 transcripts present. While GSP-1 has been physically mapped to the short arm of each of the three group 5 homoeologous chromosomes (Gill, et al., *Genetics* 143:1001–1012 (1996)), transcripts are not controlled solely by 5D. Based on these data, we consider a direct role of GSP-1 in effecting grain softness unlikely.

Northern Blot Analysis

Friabilin component transcript and protein analysis was performed on the four hard textured wheat varieties that did not contain the glycine to serine sequence change in puro B. Probes were amplified nucleic acid sequences prepared with the above puro A, puro B, and GSP 1 primers. RNA isolation, preparation of northern gel blots, and probing was done by standard methods as previously described (Giroux & Morris, *Theor. Appl. Genet.* 95:857–864 (1997)). Puro A, puro B and GSP1 probes were prepared by the random primer method (Gibco/BRL, Life Technologies Inc. Gaithersburg, Md.) to a specific activity of greater than $1 \times 10^9$ cpm/μg DNA. Two high stringency washes at 67° C. were done on each northern blot before autoradiogram exposure.

Levels of both puroindoline transcripts were found to be controlled by chromosome 5D, in that the CS Nulli 5D/Tetra 5A mRNA did not contain puroindoline transcripts and the LDN 5D(5B) mRNA did contain transcripts.

The northern blots of the mRNA from the non-serine puro B containing wheat indicated each of these four hard varieties do not contain any detectable transcripts for puro A. Transcript levels of puro B in each of these hard genotypes were similar to the soft genotypes.

C. Isolation of TRITON-X114 Soluble Proteins and Protein Electrophoresis

Friabilin components can be separated on SDS-PAGE gels into two distinct components (Morris, et al., *J. Cereal Sci.* 21:167–174 (1994)), identified as puro A and puro B. Separation of the friabilin components from "Chinese Spring" (soft), "Chinese Spring" disomic chromosome 5D substitution lines, CS-CNN DS5D (hard) ("Cheyenne" hard wheat variety as donor of the pair of 5D chromosomes), "Heron", and "Falcon" was performed.

TRITON-X100-soluble proteins were isolated by phase partitioning of TRITON-X114 (Bordier, *J. Biol. Chem.* 256:1604–1607 (1981)). Crushed whole kernels were added to 1% (v/v) TRITON-X114 in Tris Buffered Saline (TBS, 10 mM Tris, 150 mM NaCl, pH 7.5) at 4° C. and mixed for 30 min. Following a brief centrifugation(10,000×G, 5 min), the supernatant was transferred to 37° C. for 30 mm and re-centrifuged. The lower detergent phase was transferred to a new tube and the phase partitioning was repeated. Following phase partitioning, the proteins in the detergent rich phase were precipitated with 80% (v/v) acetone. Pellets were washed with acetone, ether, and dried. SDS sample buffer (no added reducing agents) was added to adjust the protein load to 1 mg whole-kernel equivalents per lane. SDS PAGE was performed by standard methods using 13.5% T, 2.6% C and 0.75 mm thick SE600 gels (Bio-Rad) and gels were silver stained by a TCA fixation method (Morris, et al., *J. Cereal Sci.* 21:167–174 (1994)).

Close examination of the bands revealed that the upper band is missing in "Falcon" and is most likely puro A since the absence of this friabilin band corresponds to the absence of the puro A transcript. This puro A band is present in all soft wheats such as "Chinese Spring" and "Heron" and all puro B serine-type hard wheat mutants, such as "Cheyenne" and the hard "Chinese Spring"/"Cheyenne" disomic substitution derivative, CS-CNN DS5D. The protein band corresponding to puro A was also absent from "Express", "Butte 86," and "Westbred 926". "Langdon" durum lacks any trace of friabilin protein, whereas substituting the pair of 5B chromosomes of "Langdon" with the 5D from "Chinese Spring" LGD-CSDS 5D(5B) restores friabilin and grain softness.

D. Transfection of Oryza Saliva With Puroindoline A and Puroindoline B Nucleic Acid Sequences by *Agrobacterium tumefaciens* Infection.

The Puroindoline A and B genes described above are used to transform rice plants. The genes are introduced into susceptible rice strains using a variation of the methods of Li, et al., *Plant Cell Rep*. 12:250–255 (1993). Briefly, co-transformation is carried out using the hygromycin construct pMON410 (from Monsanto) and a bluescript vector containing the sequences of interest. In addition, the Kpn fragment of pB822 is cloned into the pTA818 vector, which is derived from Invitrogen vector pcr1000 and contains the 1 kb fragment RAPD818. The resulting plasmid is referred to as pC822. The plants are selected on hygromycin (30mg/L) and then screened for the presence of puroindoline transcripts by northern blotting.

After the transgenic plants have produced grain, the methods described above can be used to test Xanthomonas resistance in the transformants.

E. Transformation of *Triticum aestivum* by Bombardment 12.5 μg of each DNA is coated onto gold particles for bombardment into immature wheat embryos of cultivar Bobwhite essentially as described by Weeks et al. *Plant Physiol*. 102:1077–1084 (1993) except that the embryos are incubated on callus induction media containing mannitol for 4 hours before and 20 hours after bombardment. Transformants are selected on the basis of their resistance to 1 mg/L bialaphos at the callus and green shoot stages of regeneration and to 3 mg/L bialaphos at the rooting stage of regeneration as described by Weeks et al., supra.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A grain plant comprising a recombinant nucleic acid comprising a nucleic acid selected from the group consisting of SEQ ID NO: 3 and a nucleic acid sequence that encodes a puroindoline and hybridizes to SEQ ID NO: 3 under the following conditions: hybridization at 50% formalin with 1 mg of heparin at 42° C. and a 0.2×SSC wash at 65° C. for 15 minutes, wherein the puroindoline has a glycine residue in the position corresponding to position 75 of SEQ ID NO: 4.

2. The grain plant of claim 1 wherein the grain plant is selected from the group consisting of wheat, rice, maize, barley, sorghum, triticale and oats.

3. The grain plant of claim 1 wherein the grain plant is a hexaploid wheat plant.

4. A grain plant comprising a recombinant nucleic acid encoding the amino acid sequence of SEQ ID NO: 4.

5. The grain plant of claim 4 wherein the grain plant is selected from the group consisting of wheat, rice, maize, barley, sorghum, triticale and oats.

6. The grain plant of claim 5 wherein the grain plant is a hexaploid wheat plant.

7. A method of producing a transformed cell of a grain plant comprising introducing into a cell of a grain plant a recombinant nucleic acid comprising a nucleic acid selected from the group consisting of SEQ ID NO: 3 and a nucleic acid sequence that encodes a puroindoline and hybridizes to SEQ ID NO: 3 under the following conditions: hybridization at 50% formalin with 1 mg of heparin at 42° C. and a 0.2×SSC wash at 65° C. for 15 minutes, wherein the puroindoline has a glycine residue in the position corresponding to position 75 of SEQ ID NO: 4.

8. A transformed cell of a grain plant produced by the method of claim 7.

* * * * *

SEQUENCE LISTING

```
<160> NUMBER OF SEQ ID NOS: 13

<210> SEQ ID NO 1
<211> LENGTH: 631
<212> TYPE: DNA
<213> ORGANISM: Triticum aestivum
```

```
<220> FEATURE:
<221> NAME/KEY: CDS
<222> LOCATION: (43)..(489)
<300> PUBLICATION INFORMATION:
<302> TITLE: Triticum aestivum puroindolines, two basic cystine-rich
      seed proteins: cDNA sequence analysis and developmental
      gene expression
<303> JOURNAL: Plant Mol. Biol.
<304> VOLUME: 25
<306> PAGES: 43-57
<307> DATE: 1994

<400> SEQUENCE: 1
ctcatctatt catctccacc tgcaccaaaa cacactgaca ac atg aag gcc ctc          54
                                                Met Lys Ala Leu
                                                  1 ttc ctc ata gga ctg ctt gct ctg gta gcg agc acc gcc ttt gcg caa       102
Phe Leu Ile Gly Leu Leu Ala Leu Val Ala Ser Thr Ala Phe Ala Gln
  5              10                  15                  20 tat agc gaa gtt gtt ggc agt tac gat gtt gct ggc ggg ggt ggt gct       150
Tyr Ser Glu Val Val Gly Ser Tyr Asp Val Ala Gly Gly Gly Gly Ala
             25                  30                  35 caa caa tgc cct gta gag aca aag cta aat tca tgc agg aat tac ctg       198
Gln Gln Cys Pro Val Glu Thr Lys Leu Asn Ser Cys Arg Asn Tyr Leu
         40                  45                  50 cta gat cga tgc tca acg atg aag gat ttc ccg gtc acc tgg cgt tgg       246
Leu Asp Arg Cys Ser Thr Met Lys Asp Phe Pro Val Thr Trp Arg Trp
     55                  60                  65 tgg aaa tgg tgg aag gga ggt tgt caa gag ctc ctt ggg gag tgt tgc       294
Trp Lys Trp Trp Lys Gly Gly Cys Gln Glu Leu Leu Gly Glu Cys Cys
 70                  75                  80 agt cgg ctc ggc caa atg cca ccg caa tgc cgc tgc aac atc atc cag       342
Ser Arg Leu Gly Gln Met Pro Pro Gln Cys Arg Cys Asn Ile Ile Gln
 85                  90                  95                 100 ggg tca atc caa ggc gat ctc ggt ggc atc ttc gga ttt cag cgt gat       390
Gly Ser Ile Gln Gly Asp Leu Gly Gly Ile Phe Gly Phe Gln Arg Asp
                105                 110                 115 cgg gca agc aaa gtg ata caa gaa gcc aag aac ctg ccg ccc agg tgc       438
Arg Ala Ser Lys Val Ile Gln Glu Ala Lys Asn Leu Pro Pro Arg Cys
                120                 125                 130 aac cag ggc cct ccc tgc aac atc ccc ggc act att ggc tat tac tgg       486
Asn Gln Gly Pro Pro Cys Asn Ile Pro Gly Thr Ile Gly Tyr Tyr Trp
            135                 140                 145 tga tgtagcttcc atttatgact agctaataaa ctgtcacata ccactgcgtg            539
tgacaaataa aagtggtcat ggaataattt atgaataaaa tttcagcatg tgcctgcgcg     599
aggtgtctat agcaaaaaaa aaaaaaaaaa aa                                   631

<210> SEQ ID NO 2
<211> LENGTH: 148
<212> TYPE: PRT
<213> ORGANISM: Triticum aestivum

<400> SEQUENCE: 2

Met Lys Ala Leu Phe Leu Ile Gly Leu Leu Ala Leu Val Ala Ser Thr
  1               5                  10                  15

Ala Phe Ala Gln Tyr Ser Glu Val Val Gly Ser Tyr Asp Val Ala Gly
             20                  25                  30

Gly Gly Gly Ala Gln Gln Cys Pro Val Glu Thr Lys Leu Asn Ser Cys
         35                  40                  45

Arg Asn Tyr Leu Leu Asp Arg Cys Ser Thr Met Lys Asp Phe Pro Val
     50                  55                  60
```

```
Thr Trp Arg Trp Trp Lys Trp Trp Lys Gly Gly Cys Gln Glu Leu Leu
        65                  70                  75                  80

Gly Glu Cys Cys Ser Arg Leu Gly Gln Met Pro Pro Gln Cys Arg Cys
                85                  90                  95

Asn Ile Ile Gln Gly Ser Ile Gln Gly Asp Leu Gly Gly Ile Phe Gly
            100                 105                 110

Phe Gln Arg Asp Arg Ala Ser Lys Val Ile Gln Glu Ala Lys Asn Leu
        115                 120                 125

Pro Pro Arg Cys Asn Gln Gly Pro Pro Cys Asn Ile Pro Gly Thr Ile
    130                 135                 140

Gly Tyr Tyr Trp
145

<210> SEQ ID NO 3
<211> LENGTH: 598
<212> TYPE: DNA
<213> ORGANISM: Triticum aestivum
<220> FEATURE:
<221> NAME/KEY: CDS
<222> LOCATION: (17)..(463)
<300> PUBLICATION INFORMATION:
<302> TITLE: Triticum aestivum puroindolines, two basic cystine-rich
      seed proteins: cDNA sequence analysis and developmental
      gene expression
<303> JOURNAL: Plant Mol. Biol.
<304> VOLUME: 25
<306> PAGES: 43-57
<307> DATE: 1994

<400> SEQUENCE: 3
aaacaacatt gaaaac atg aag acc tta ttc ctc cta gct ctc ctt gct ctt    52
               Met Lys Thr Leu Phe Leu Leu Ala Leu Leu Ala Leu
                 1               5                  10 gta gcg agc aca acc ttc gcg caa tac tca gaa gtt ggc ggc tgg tac   100
Val Ala Ser Thr Thr Phe Ala Gln Tyr Ser Glu Val Gly Gly Trp Tyr
         15                  20                  25 aat gaa gtt ggc gga gga ggt ggt tct caa caa tgt ccg cag gag cgg   148
Asn Glu Val Gly Gly Gly Gly Ser Gln Gln Cys Pro Gln Glu Arg
    30                  35                  40 ccg aag cta agc tct tgc aag gat tac gtg atg gag cga tgt ttc aca   196
Pro Lys Leu Ser Ser Cys Lys Asp Tyr Val Met Glu Arg Cys Phe Thr
 45                  50                  55                  60 atg aag gat ttt cca gtc acc tgg ccc aca aaa tgg tgg aag ggc ggc   244
Met Lys Asp Phe Pro Val Thr Trp Pro Thr Lys Trp Trp Lys Gly Gly
                 65                  70                  75 tgt gag cat gag gtt cgg gag aag tgc tgc aag cag ctg agc cag ata   292
Cys Glu His Glu Val Arg Glu Lys Cys Cys Lys Gln Leu Ser Gln Ile
             80                  85                  90 gca cca caa tgt cgc tgt gat tct atc cgg cga gtg atc caa ggc agg   340
Ala Pro Gln Cys Arg Cys Asp Ser Ile Arg Arg Val Ile Gln Gly Arg
         95                 100                 105 ctc ggt ggc ttc ttg ggc att tgg cga ggt gag gta ttc aaa caa ctt   388
Leu Gly Gly Phe Leu Gly Ile Trp Arg Gly Glu Val Phe Lys Gln Leu
    110                 115                 120 cag agg gcc cag agc ctc ccc tca aag tgc aac atg ggc gcc gac tgc   436
Gln Arg Ala Gln Ser Leu Pro Ser Lys Cys Asn Met Gly Ala Asp Cys
125                 130                 135                 140 aag ttc cct agt ggc tat tac tgg tga tatagcc tctattcgtg           483
Lys Phe Pro Ser Gly Tyr Tyr Trp
                145 ccaataaaat gtcacatatc atagcaagtg gcaaataaga gtgctgagtg atgatctatg   543
```

```
aataaaatca cccttgtata ttgatctgtg ttcgagaaaa aaaaaaaaaa aaaaa            598
```

<210> SEQ ID NO 4
<211> LENGTH: 148
<212> TYPE: PRT
<213> ORGANISM: Triticum aestivum

<400> SEQUENCE: 4

```
Met Lys Thr Leu Phe Leu Leu Ala Leu Leu Ala Leu Val Ala Ser Thr
 1               5                  10                  15

Thr Phe Ala Gln Tyr Ser Glu Val Gly Gly Trp Tyr Asn Glu Val Gly
            20                  25                  30

Gly Gly Gly Ser Gln Gln Cys Pro Gln Glu Arg Pro Lys Leu Ser
        35                  40                  45

Ser Cys Lys Asp Tyr Val Met Glu Arg Cys Phe Thr Met Lys Asp Phe
    50                  55                  60

Pro Val Thr Trp Pro Thr Lys Trp Trp Lys Gly Gly Cys Glu His Glu
65                  70                  75                  80

Val Arg Glu Lys Cys Cys Lys Gln Leu Ser Gln Ile Ala Pro Gln Cys
                85                  90                  95

Arg Cys Asp Ser Ile Arg Arg Val Ile Gln Gly Arg Leu Gly Gly Phe
            100                 105                 110

Leu Gly Ile Trp Arg Gly Glu Val Phe Lys Gln Leu Gln Arg Ala Gln
        115                 120                 125

Ser Leu Pro Ser Lys Cys Asn Met Gly Ala Asp Cys Lys Phe Pro Ser
    130                 135                 140

Gly Tyr Tyr Trp
145
```

<210> SEQ ID NO 5
<211> LENGTH: 598
<212> TYPE: DNA
<213> ORGANISM: Triticum aestivum
<220> FEATURE:
<221> NAME/KEY: CDS
<222> LOCATION: (17)..(463)

<400> SEQUENCE: 5

```
aaacaacatt gaaaac atg aag acc tta ttc ctc cta gct ctc ctt gct ctt      52
               Met Lys Thr Leu Phe Leu Leu Ala Leu Leu Ala Leu
                1               5                  10 gta gcg agc aca acc ttc gcg caa tac tca gaa gtt ggc ggc tgg tac      100
Val Ala Ser Thr Thr Phe Ala Gln Tyr Ser Glu Val Gly Gly Trp Tyr
            15                  20                  25 aat gaa gtt ggc gga gga ggt ggt tct caa caa tgt ccg cag gag cgg      148
Asn Glu Val Gly Gly Gly Gly Ser Gln Gln Cys Pro Gln Glu Arg
        30                  35                  40 ccg aag cta agc tct tgc aag gat tac gtg atg gag cga tgt ttc aca      196
Pro Lys Leu Ser Ser Cys Lys Asp Tyr Val Met Glu Arg Cys Phe Thr
45                  50                  55                  60 atg aag gat ttt cca gtc acc tgg ccc aca aaa tgg tgg aag agc ggc      244
Met Lys Asp Phe Pro Val Thr Trp Pro Thr Lys Trp Trp Lys Ser Gly
                65                  70                  75 tgt gag cat gag gtt cgg gag aag tgc tgc aag cag ctg agc cag ata      292
Cys Glu His Glu Val Arg Glu Lys Cys Cys Lys Gln Leu Ser Gln Ile
            80                  85                  90 gca cca caa tgt cgc tgt gat tct atc cgg cga gtg atc caa ggc agg      340
Ala Pro Gln Cys Arg Cys Asp Ser Ile Arg Arg Val Ile Gln Gly Arg
        95                  100                 105
```

```
ctc ggt ggc ttc ttg ggc att tgg cga ggt gag gta ttc aaa caa ctt    388
Leu Gly Gly Phe Leu Gly Ile Trp Arg Gly Glu Val Phe Lys Gln Leu
        110                 115                 120 cag agg gcc cag agc ctc ccc tca aag tgc aac atg ggc gcc gac tgc    436
Gln Arg Ala Gln Ser Leu Pro Ser Lys Cys Asn Met Gly Ala Asp Cys
125                 130                 135                 140 aag ttc cct agt ggc tat tac tgg tga tgatatagcc tctattcgtg          483
Lys Phe Pro Ser Gly Tyr Tyr Trp
                145 ccaataaaat gtcacatatc atagcaagtg gcaaataaga gtgctgagtg atgatctatg  543 aataaaatca cccttgtata ttgatctgtg ttcgagaaaa aaaaaaaaaa aaaaa       598

<210> SEQ ID NO 6
<211> LENGTH: 148
<212> TYPE: PRT
<213> ORGANISM: Triticum aestivum

<400> SEQUENCE: 6

Met Lys Thr Leu Phe Leu Leu Ala Leu Leu Ala Leu Val Ala Ser Thr
  1               5                  10                  15

Thr Phe Ala Gln Tyr Ser Glu Val Gly Gly Trp Tyr Asn Glu Val Gly
             20                  25                  30

Gly Gly Gly Gly Ser Gln Gln Cys Pro Gln Glu Arg Pro Lys Leu Ser
         35                  40                  45

Ser Cys Lys Asp Tyr Val Met Glu Arg Cys Phe Thr Met Lys Asp Phe
     50                  55                  60

Pro Val Thr Trp Pro Thr Lys Trp Trp Lys Ser Gly Cys Glu His Glu
 65                  70                  75                  80

Val Arg Glu Lys Cys Cys Lys Gln Leu Ser Gln Ile Ala Pro Gln Cys
                 85                  90                  95

Arg Cys Asp Ser Ile Arg Arg Val Ile Gln Gly Arg Leu Gly Gly Phe
            100                 105                 110

Leu Gly Ile Trp Arg Gly Glu Val Phe Lys Gln Leu Gln Arg Ala Gln
        115                 120                 125

Ser Leu Pro Ser Lys Cys Asn Met Gly Ala Asp Cys Lys Phe Pro Ser
    130                 135                 140

Gly Tyr Tyr Trp
145

<210> SEQ ID NO 7
<211> LENGTH: 19
<212> TYPE: DNA
<213> ORGANISM: Triticum aestivum

<400> SEQUENCE: 7
atgaaggccc tcttcctca                                                19

<210> SEQ ID NO 8
<211> LENGTH: 22
<212> TYPE: DNA
<213> ORGANISM: Triticum aestivum

<400> SEQUENCE: 8
tcaccagtaa tagccaatag tg                                            22

<210> SEQ ID NO 9
<211> LENGTH: 21
<212> TYPE: DNA
```

-continued

```
<213> ORGANISM: Triticum aestivum

<400> SEQUENCE: 9
atgaagacct tattcctcct a                                           21

<210> SEQ ID NO 10
<211> LENGTH: 24
<212> TYPE: DNA
<213> ORGANISM: Triticum aestivum

<400> SEQUENCE: 10
tcaccagtaa tagccactag ggaa                                        24

<210> SEQ ID NO 11
<211> LENGTH: 24
<212> TYPE: DNA
<213> ORGANISM: Triticum aestivum

<400> SEQUENCE: 11
ccaccagtaa tagccactag ggaa                                        24

<210> SEQ ID NO 12
<211> LENGTH: 20
<212> TYPE: DNA
<213> ORGANISM: Triticum aestivum

<400> SEQUENCE: 12
gtagtgagca ctactattgc                                             20

<210> SEQ ID NO 13
<211> LENGTH: 19
<212> TYPE: DNA
<213> ORGANISM: Triticum aestivum

<400> SEQUENCE: 13
gagccttccc tccaagtgc                                              19
```